US010695518B2

(12) United States Patent
Weaver et al.

(10) Patent No.: US 10,695,518 B2
(45) Date of Patent: Jun. 30, 2020

(54) ORAL CANNULA

(71) Applicant: ANESTHEMED, LLC, New Albany, OH (US)

(72) Inventors: Wendy Weaver, Arnold, MD (US); Glen Weaver, Murrysville, PA (US); Peter Stoelzle, Galena, OH (US); Michael Medors, Johnstown, OH (US); Boon Pheng Tang, Galena, OH (US)

(*) Notice: Subject to any disclaimer, the term of this patent is extended or adjusted under 35 U.S.C. 154(b) by 1083 days.

(21) Appl. No.: 15/094,562

(22) Filed: Apr. 8, 2016

(65) Prior Publication Data

US 2016/0220777 A1    Aug. 4, 2016

Related U.S. Application Data

(63) Continuation-in-part of application No. 14/498,006, filed on Sep. 26, 2014, now Pat. No. 9,993,607.
(Continued)

(51) Int. Cl.
*A61M 16/08*     (2006.01)
*A61M 16/04*     (2006.01)
(Continued)

(52) U.S. Cl.
CPC ......... *A61M 16/085* (2014.02); *A61B 5/0836* (2013.01); *A61B 5/097* (2013.01); *A61B 5/4839* (2013.01); *A61M 16/0463* (2013.01); *A61M 16/0488* (2013.01); *A61M 16/0666* (2013.01); *A61B 2010/0083* (2013.01); *A61M 16/0418* (2014.02); *A61M 2202/0208* (2013.01); *A61M 2210/0625* (2013.01); *A61M 2230/432* (2013.01)

(58) Field of Classification Search
CPC ............ A61M 16/085; A61M 16/0463; A61M 16/0488; A61M 16/0666; A61M 16/0418; A61M 2202/0208; A61M 2210/0625; A61M 2230/432; A61B 5/0836; A61B 5/097; A61B 5/4839; A61B 2010/0083
See application file for complete search history.

(56) References Cited

U.S. PATENT DOCUMENTS 3,590,820 A    7/1971  Nehra et al.
3,593,713 A *  7/1971  Bogoff ............. A61M 25/0017
                                                604/102.02
(Continued)

*Primary Examiner* — Timothy A Stanis
*Assistant Examiner* — Jonathan S Paciorek
(74) *Attorney, Agent, or Firm* — Michael J. Gallagher, Esq.; Luper Neidenthal & Logan, LPA

(57) ABSTRACT

An oral cannula for placement within the oral cavity of a patient for delivery of a treatment gas and for collecting end-tidal carbon dioxide ($ETCO_2$) includes a treatment gas delivery lumen including at least one aperture near a distal end of the treatment gas delivery lumen; an end-tidal $CO_2$ sampling lumen. The cannula also includes a cap having (i) a gas diverter adapted for diverting at least a portion of the treatment gas and (ii) an end-tidal $CO_2$ inlet including flutes and apertures there between that are in communication with the end-tidal $CO_2$ sampling lumen. The oral cannula is adapted for custom bending or has a bend such that the oral cannula is insertable and retainable in a patient's mouth and functional for supplying a treatment gas and sampling gas exhaled by the patient.

26 Claims, 19 Drawing Sheets

Related U.S. Application Data

(60) Provisional application No. 61/886,646, filed on Oct. 3, 2013, provisional application No. 62/009,522, filed on Jun. 9, 2014.

(51) Int. Cl.
    *A61B 5/00*     (2006.01)
    *A61B 5/097*     (2006.01)
    *A61B 5/083*     (2006.01)
    *A61M 16/06*     (2006.01)
    *A61B 10/00*     (2006.01)

(56) References Cited

U.S. PATENT DOCUMENTS

| | | | |
|---|---|---|---|
| 3,957,055 A | 5/1976 | Linder et al. | |
| 4,502,482 A * | 3/1985 | DeLuccia | A61M 16/04 |
| | | | 128/207.14 |
| 4,595,005 A | 6/1986 | Jinotti | |
| 4,662,871 A | 5/1987 | Rafelson | |
| 5,335,656 A | 8/1994 | Bowe et al. | |
| 5,544,648 A | 8/1996 | Fischer, Jr. | |
| 5,690,487 A | 11/1997 | Whitehouse et al. | |
| 5,788,680 A | 8/1998 | Linder | |
| 6,439,234 B1 | 8/2002 | Curti et al. | |
| 6,729,334 B1 * | 5/2004 | Baran | A61M 16/0463 |
| | | | 128/200.14 |
| 7,273,050 B2 * | 9/2007 | Wei | A61M 16/04 |
| | | | 128/200.26 |
| 2005/0217678 A1 | 10/2005 | McCormick et al. | |
| 2007/0215162 A1 | 9/2007 | Glassenberg et al. | |
| 2010/0139664 A1 | 6/2010 | Curti et al. | |
| 2012/0209096 A1 | 8/2012 | Jaffe et al. | |
| 2012/0271187 A1 | 10/2012 | McNeill | |

* cited by examiner

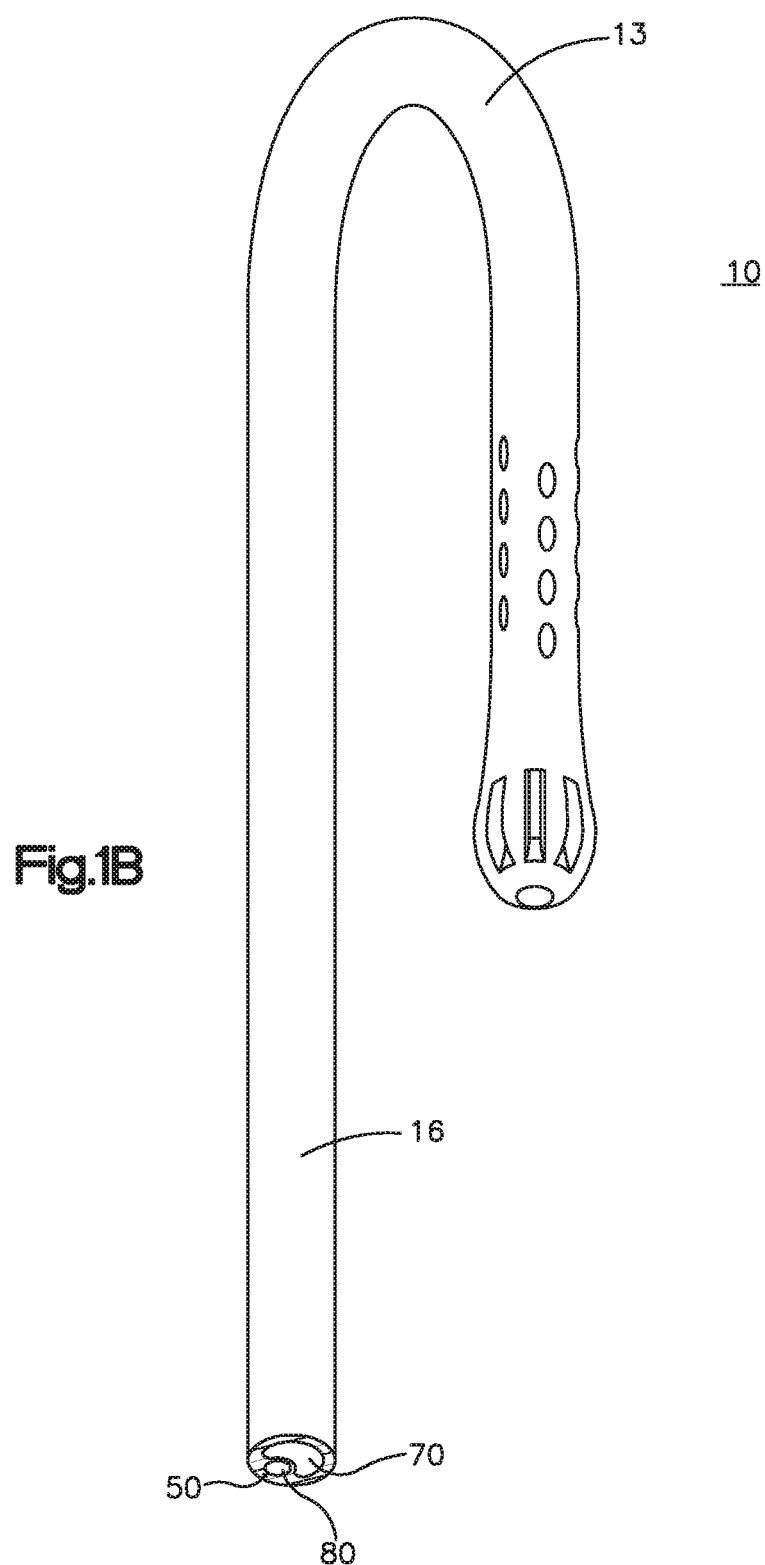

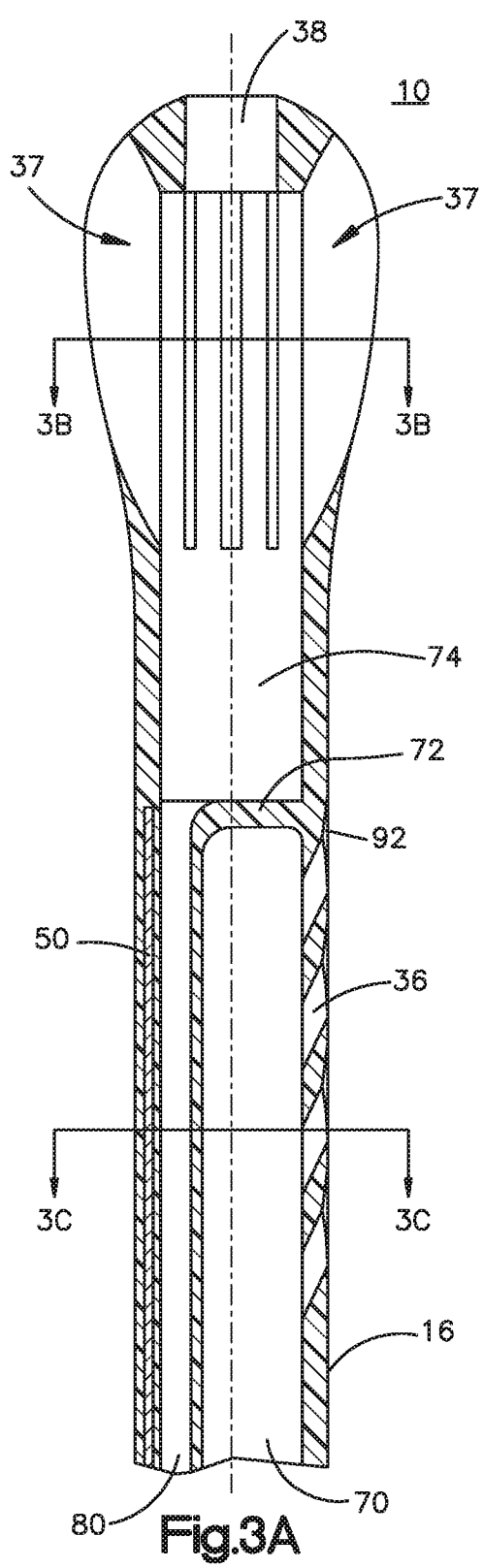
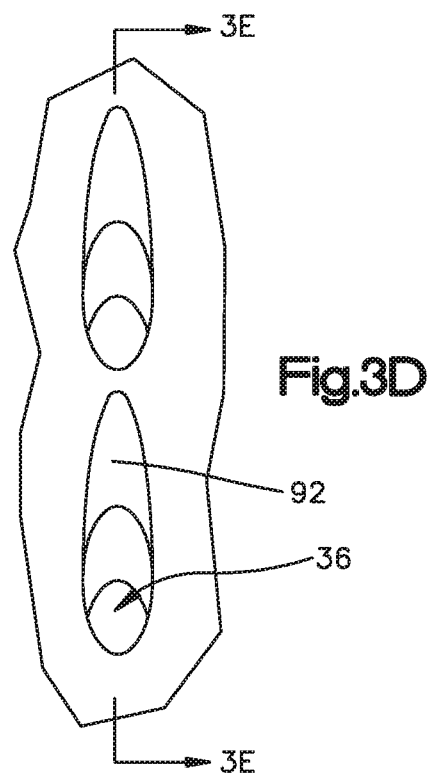
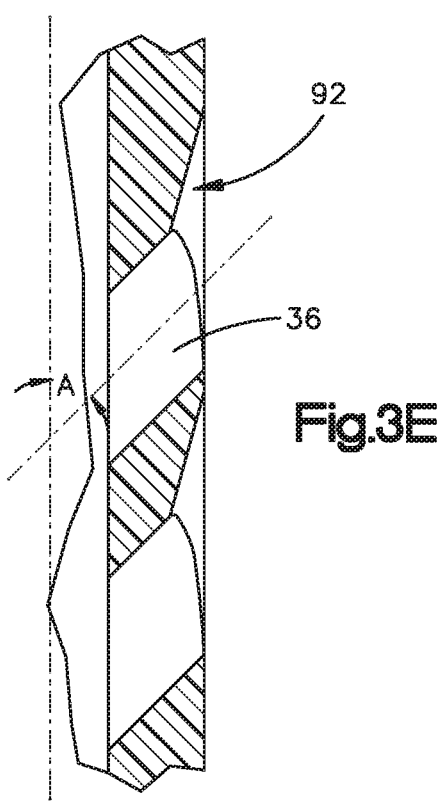

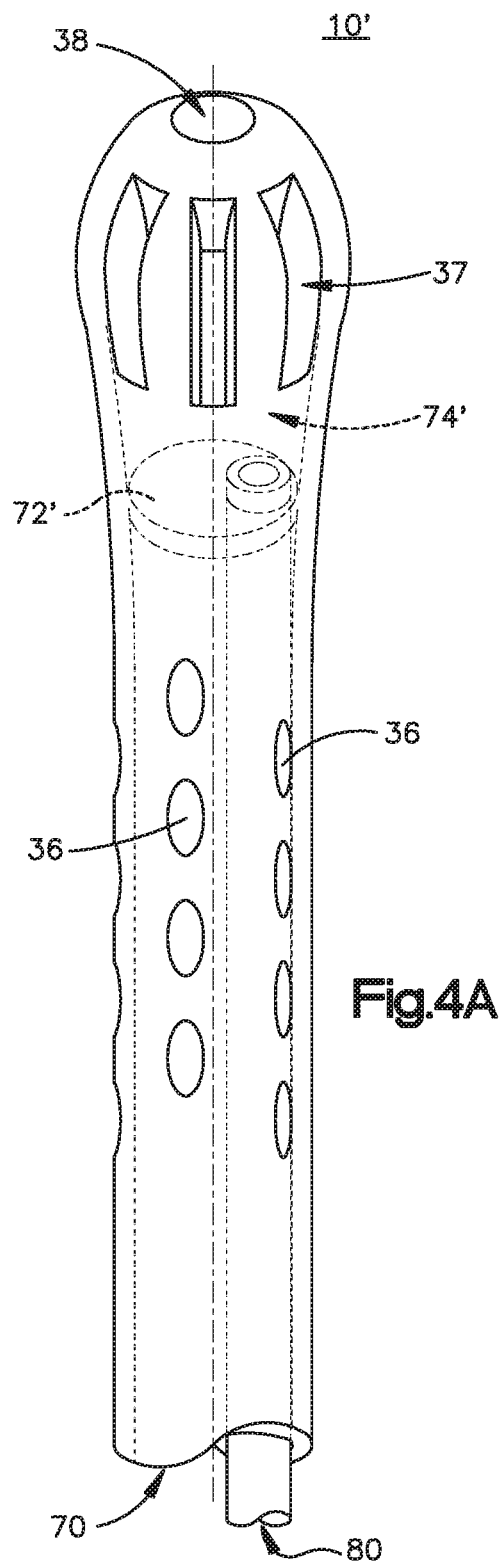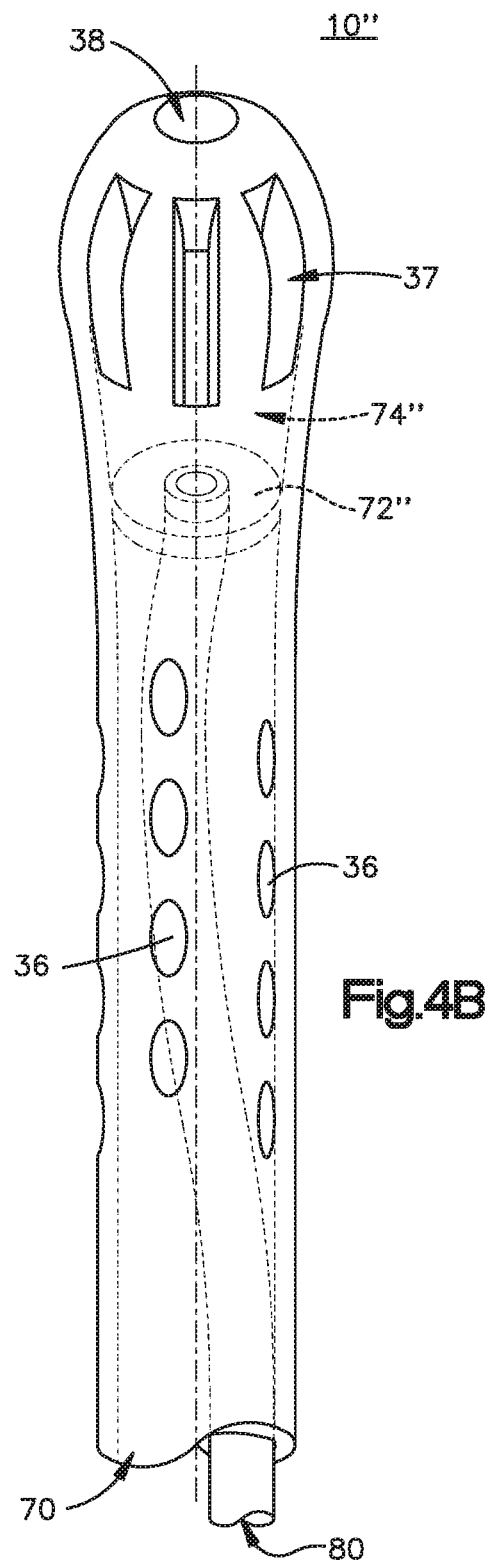

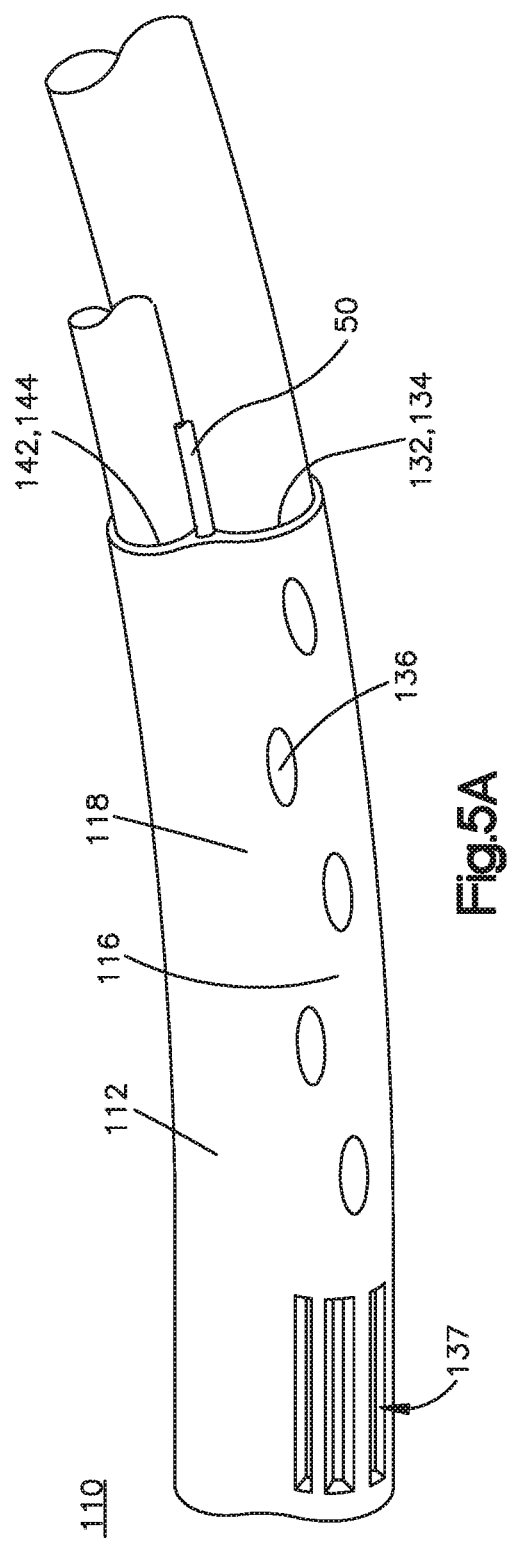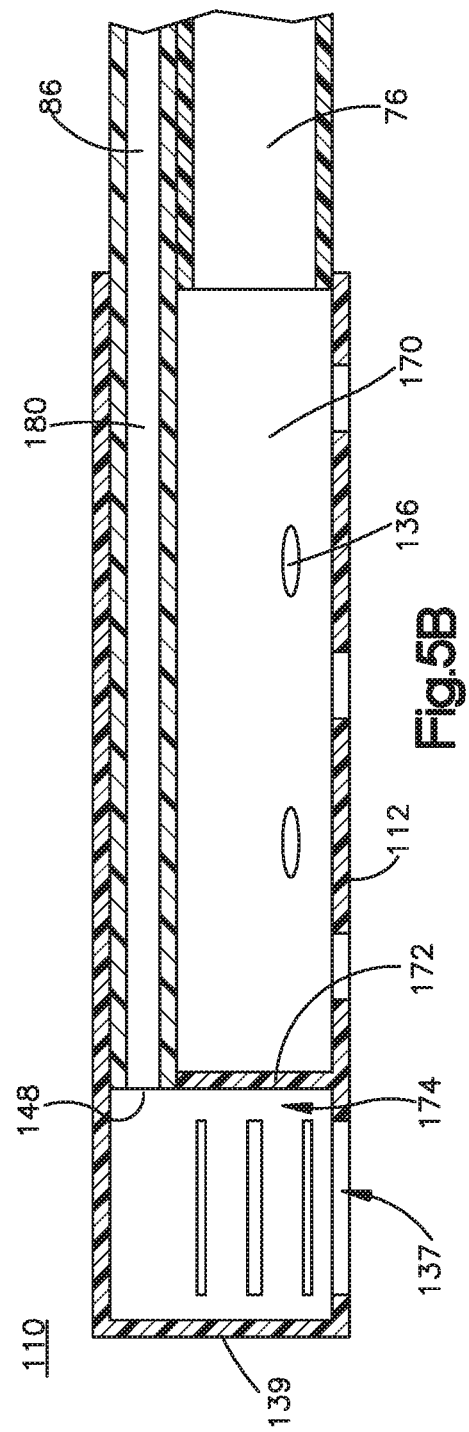

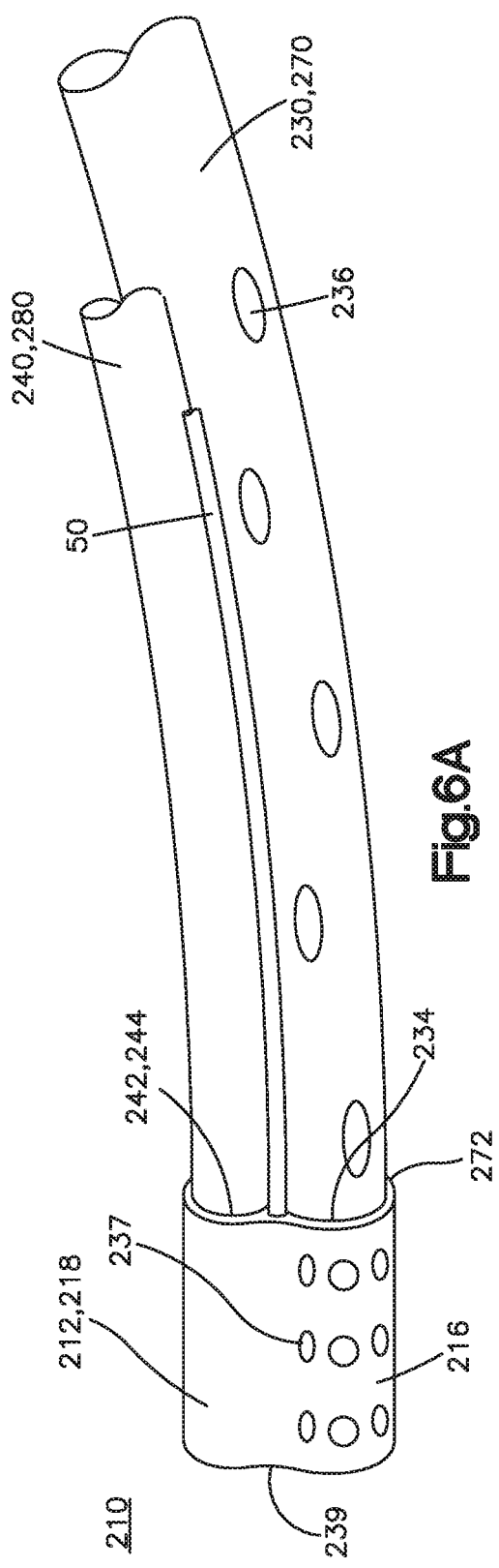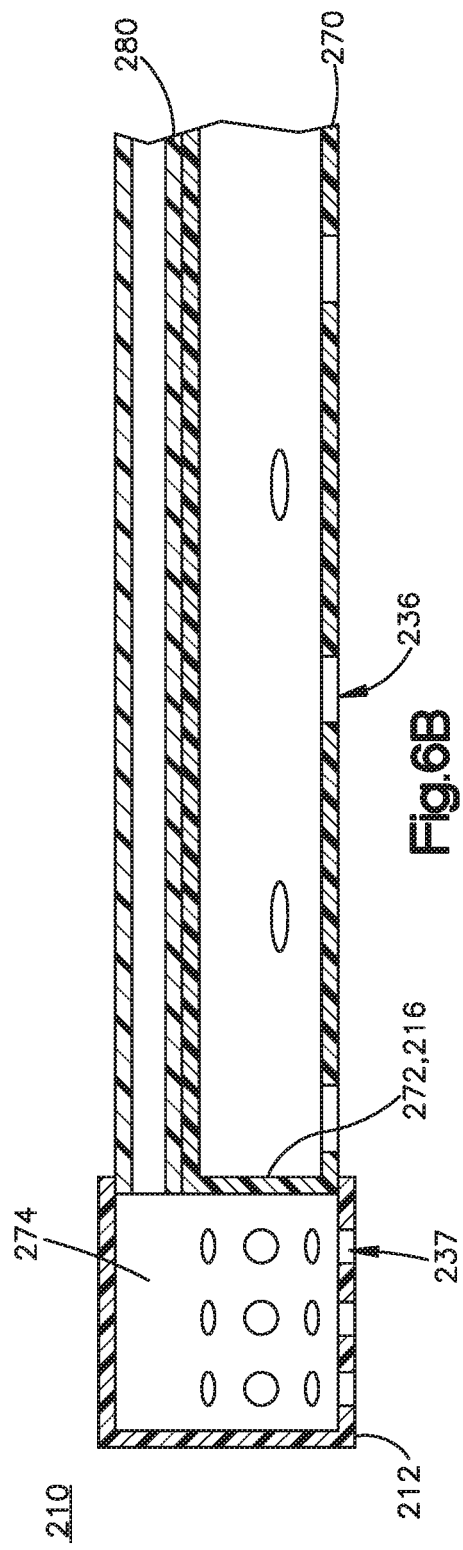

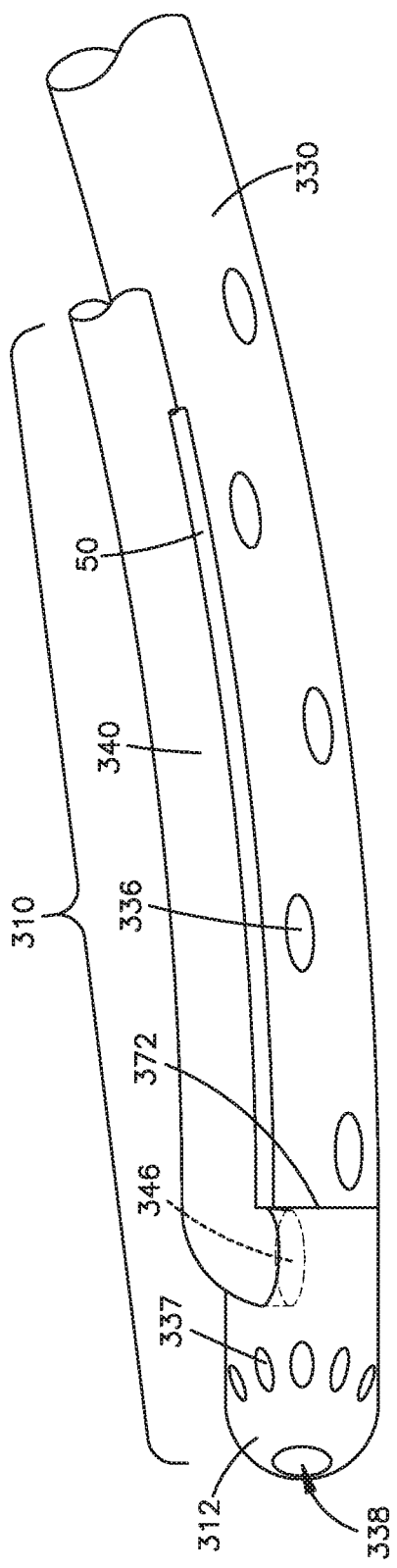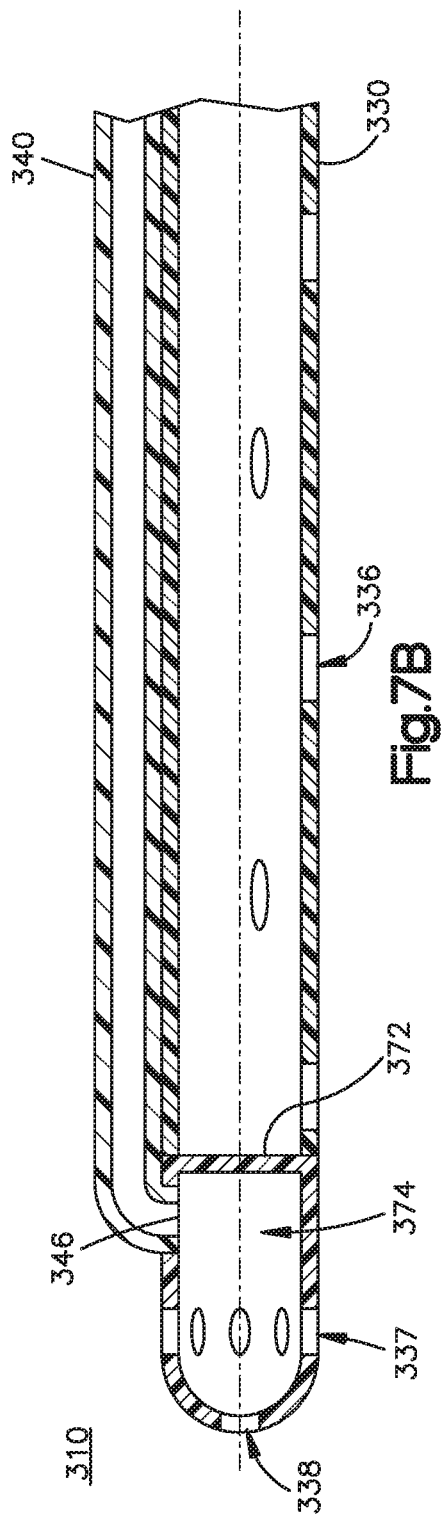

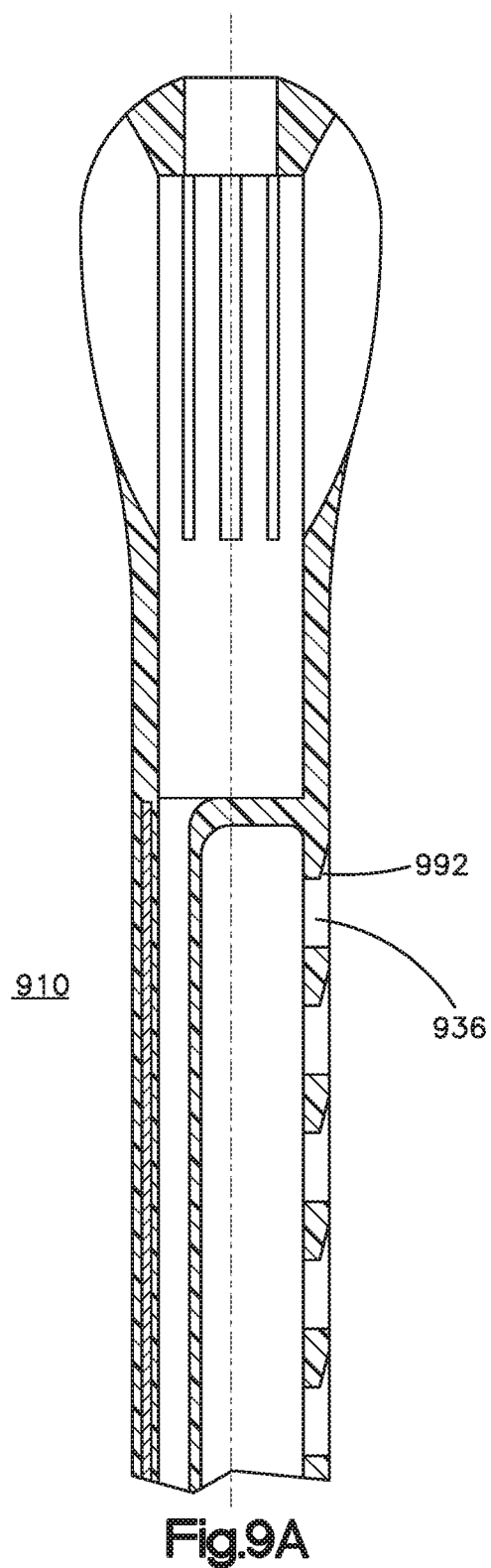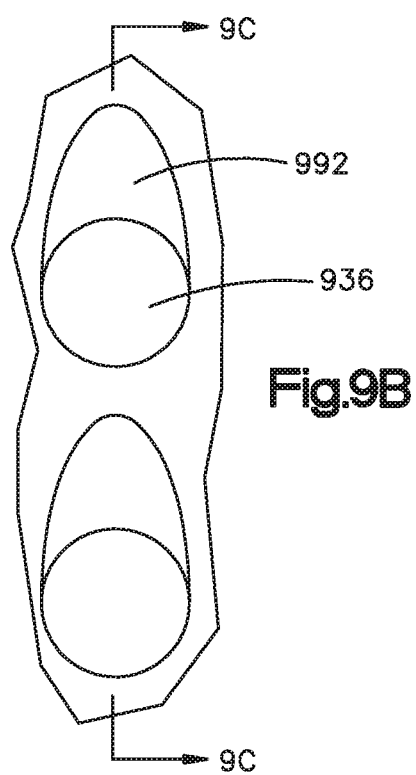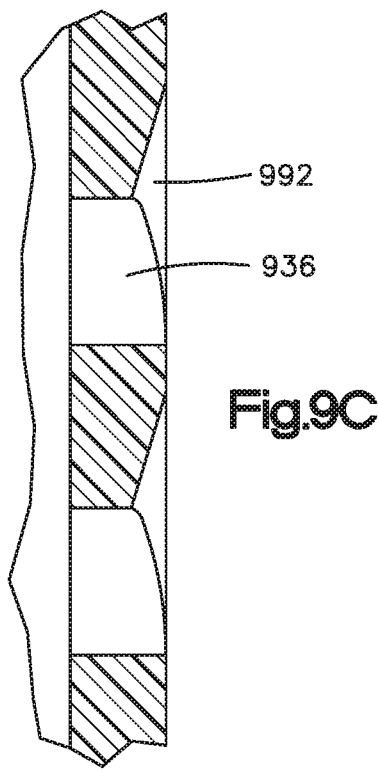

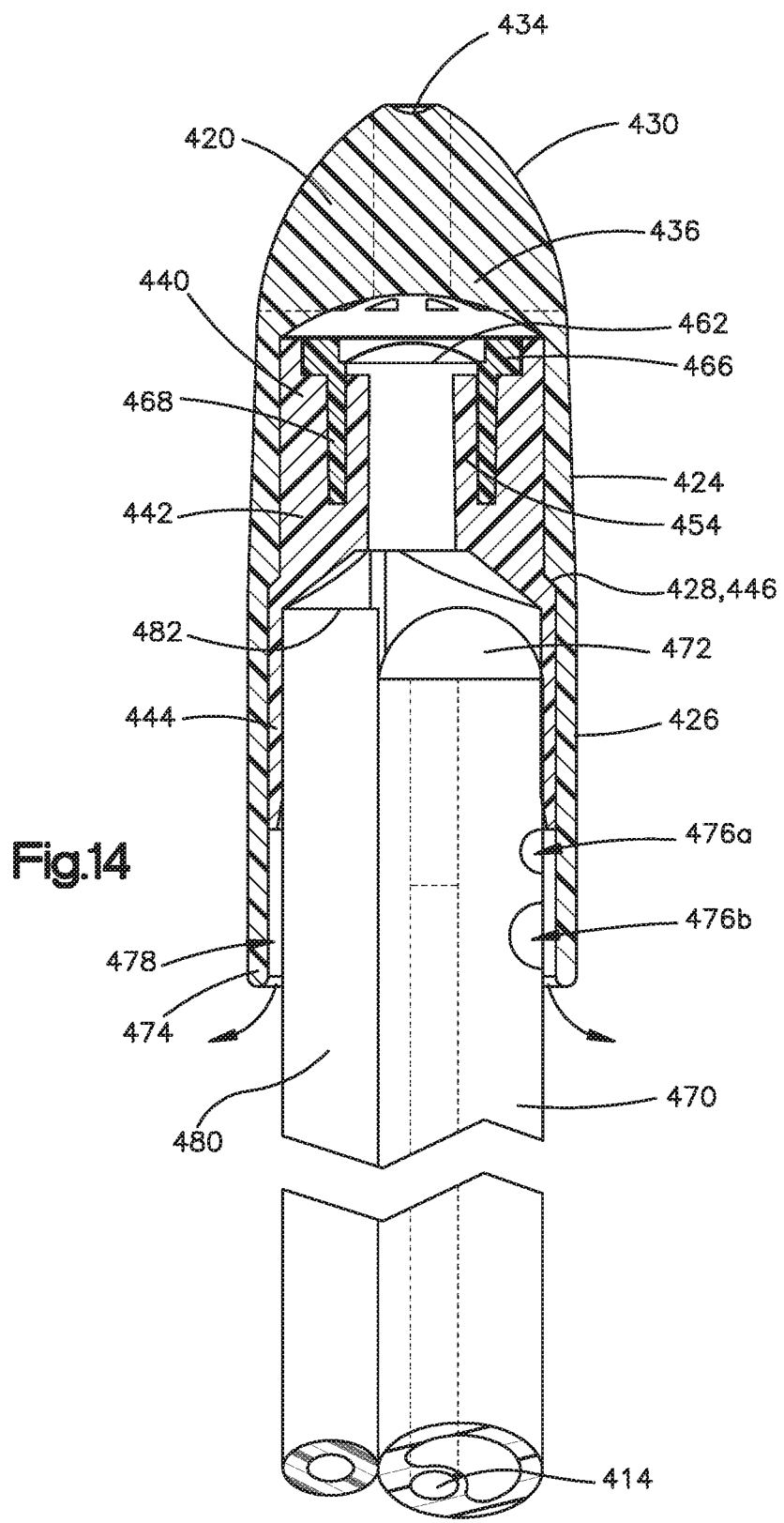

ORAL CANNULA

CROSS-REFERENCE TO RELATED APPLICATIONS

This application is a continuation-in-part of U.S. patent application Ser. No. 14/498,006, filed Sep. 26, 2014, which claims priority to U.S. Provisional Application No. 61/886,646, filed Oct. 3, 2013, and U.S. Provisional Application No. 62/009,522, filed Jun. 9, 2014, the disclosures of which are incorporated herein by reference in their entireties.

BACKGROUND

The present invention relates to medical devices and methods, and more particularly to medical devices and methods used while a patient is anesthetized.

Continuous monitoring of exhaled carbon dioxide ($CO_2$), referred to as capnography, is the conventional standard of care for monitoring a patient's ventilation during operating room procedures. Capnography is also often used during non-intubated procedures that use moderate or deep sedation. A popular means for capnography is the well-known nasal cannula, such as disclosed in U.S. Pat. Nos. 5,335,656 and 6,439,234, which uses one nasal tube to supply oxygen ($O_2$) to the sedated patient and another nasal tube to draw end-tidal carbon dioxide ($ETCO_2$) for monitoring. A conventional Nasal Cannula (Adult) Salter Style® Ref. 4707F from Salter Labs is packaged with several feet of side-by-side oxygen supply tubing and sampling lumen tubing, which terminates at individual, free tubes that are connected to opposing sides of the nasal cannula body.

Typically, the tubes connected to opposing ends of the nasal cannula are looped over the patient's ears, and then the tubes merge into a side-by-side configuration that extends to the oxygen supply and capnography system Under certain conditions, the sedated patient may receive insufficient oxygen through the nasal passages, such as when the nasal passages are blocked. An anesthetist might then place the nasal cannula in the patient's mouth, such as through a portion of a bite block (if present) and increase the oxygen flow.

SUMMARY

As described herein, an oral cannula for delivering oxygen and sampling end-tidal carbon dioxide includes an oxygen supply lumen having plural outlets near a distal end of the oxygen supply lumen. The oral cannula also includes an end-tidal carbon dioxide ($ETCO_2$) lumen having an inlet near a distal end of the $ETCO_2$ lumen. The $ETCO_2$ lumen and oxygen supply lumen form a unitary oral cannula such that the oxygen supply lumen outlet is spaced apart from the $ETCO_2$ lumen inlet. The oral cannula is adapted for bending or has a bend such that the oral cannula is insertable and retainable in a patient's mouth.

In one embodiment, a method of administering oxygen and sampling end-tidal ET $ETCO_2$ for a patient includes a step of providing oxygen through an oxygen supply tube and through an outlet near a distal end of the oxygen supply tube. The method also includes a step of drawing a gas sample through an $ETCO_2$ tube and through an inlet near a distal end of the $ETCO_2$ tube. The $ETCO_2$ tube is affixed to the oxygen supply tube to form a unitary oral cannula, such that the oxygen tube outlet is spaced apart from the $ETCO_2$ inlet.

Structures disclosed in parent U.S. patent application Ser. No. 14/498,006 in testing has performed adequately. The inventors have discovered unexpected aspects of the function of the structure disclosed in the parent application, which discoveries have led to the new configurations disclosed herein. The present disclosure is not intended to disclaim subject matter in the parent application, as the configurations in the parent application have merit and are operable depending on the particular application of the device.

The inventors discovered that under some circumstances, with oxygen supply pressures and volumetric flow rates common to modem practice, a structure disclosed in the parent application was found to unexpectedly interfere with the collection of $ETCO_2$. The structure and location of the $O_2$ gas outlet apertures in the parent were designed to direct treatment gas deep into the oral cavity, a seemingly desirable effect. However, by directing the $O_2$ to the back of the mouth so that it can be readily delivered, it was discovered that the $O_2$ could also more readily mix with the $ETCO_2$ being expelled from the mouth under some testing conditions. As a result, the $O_2$ treatment gas had an unexpected dilutive effect upon the $ETCO_2$ being collected by the $ETCO_2$ sample lumen. The resulting gas mixture analyzed by the monitoring equipment (i.e. capnograph) did not represent the true concentration of $ETCO_2$ being expired. This dilutive effect was further amplified when higher $O_2$ flow rates are required, typically during deep sedation.

Further, the inventors discovered that under some circumstances, the oxygen gas outlet apertures sub-optimally deliver oxygen. In this regard, in some configurations disclosed in the parent application, most of the delivered treatment gas exits from the outlet nearest the closed end of the delivery tube (where resistance is first encountered). In some configurations, as much as 90% of the volumetric flow rate occurred through the outlet nearest the distal end. This occurs despite the fact that all of the treatment gas holes are of uniform size. The magnitude of the uneven flow rates across the apertures was surprising. Thus, the outlet apertures with low flow rate more readily allow for entry of body fluids (i.e. saliva, blood, phlegm, etc.) into the lumen, possibly causing treatment gas flow disturbance. Contamination of the oxygen path (flow meter, pressure regulator, etc.) is also possible. The uneven gas flow might also affect $ETCO_2$ sampling, described above.

The inventors have also discovered that in practice, under some circumstances, the structure of the $ETCO_2$ sampling apertures can collect body fluids (i.e. saliva, blood, phlegm, etc.). When sufficient volume of fluid is collected, an occlusion of the sampling lumen or tubing may occur. The inventors have also discovered that in practice under some circumstances, $ETCO_2$ sampling may be diminished by mucus and saliva and in general sought to improve the structure and function of the sampling inlet when in contact with mucosal tissue and other obstructions within the oral cavity (i.e. the tongue, palate, etc.).

In general, without the explanation intending to limit the scope of the claims, the inventors addressed their observations and discoveries by employing flutes at the tip of the oral cannula, by employing a hydrophobic filter, and by employing a gas diverter. The present invention is not limited to having each of these features, as the claims are intended to define the scope of the invention.

A preferred embodiment employs a single fluted tip to help redirect bodily fluids away from the sampling lumen and diminish the likelihood of blockage caused by contact with mucosal tissue and other obstructions within the oral cavity. A hydrophobic filter is located (preferably immediately behind or proximal to) below the $ETCO_2$ sampling aperture as an additional means for protecting the $ETCO_2$ sampling gas line from occluding. The combination of protective flutes and hydrophobic filter offers redundant means of inhibiting obstruction of $ETCO_2$ sampling gas flows. An end cap diverter is designed to deliver treatment gas, such as $O_2$, flowing from the treatment gas exit apertures toward the front of the oral cavity rather than the rear. In part, the purpose of the diverter is to segregate the oxygen gas from the $ETCO_2$ gas which is being simultaneously collected and returned to the monitoring equipment. As the treatment gas flows from the treatment gas exit apertures, its path is redirected at approximately 90 degrees from its exit direction and approximately 180 degrees from its supply direction through the lumen by the end cap diverter, and thus toward the front of the oral cavity. In this regard the gas exits the diverter in a counter-flow orientation relative to the flow through the delivery lumen. Further, the disparity in gas volume flow rates is reduced by limiting the number and changing the size of delivery gas apertures.

In some embodiments, an oral cannula for placement within the oral cavity of a patient for delivery of a treatment gas and for collecting $ETCO_2$ includes a treatment gas delivery lumen including at least one oropharyngeal aperture near a distal end of the treatment gas delivery lumen; an exhaled gas sampling lumen. The cannula also includes a cap having (i) a gas diverter adapted for diverting at least a portion of the treatment gas and (ii) an exhaled gas inlet including flutes and apertures there between that are in communication with the exhaled gas sampling lumen. The oral cannula is adapted for custom bending or has a bend such that the oral cannula is insertable and retainable in a patient's mouth and functional for supplying a treatment gas and sampling gas exhaled by the patient.

In some embodiments, the oral cannula may include a hydrophobic filter in the end-tidal $CO_2$ sampling lumen. The oral cannula may also include a filter housing located in the cap and housing the hydrophobic filter. The filter housing may be rigid and thereby provide radial rigidity to the cap. In some embodiments, the gas diverter is a skirt at a periphery of the proximal end of the cap. The skirt may form a plenum into which at least one aperture in the treatment gas delivery lumen opens. The filter housing may provide rigidity to the skirt to inhibit occlusion of at least one aperture in the gas delivery lumen. In some embodiments, the skirt is continuous about the cap. The cap may include a body and a funnel that is housed within the body, and the filter housing may be mounted to the funnel. The cap may include an end-tidal $CO_2$ sampling channel between the end-tidal $CO_2$ inlets and the end-tidal $CO_2$ sampling lumen, the filter being disposed in the end-tidal $CO_2$ sampling channel. The rigid filter housing may be adapted for resisting occlusion of the end-tidal $CO_2$ sampling lumen channel. The cap may include a sampling recess and a delivery recess on a proximal end thereof. The end-tidal $CO_2$ sampling lumen may be located in the sampling recess. The treatment gas delivery lumen may be located in the delivery recess. The cap may be cylindrical. The flutes may form the distal-most portion of the cap. The filter may be at a base of the flutes.

In some embodiments, the oral cannula includes a shaping wire that is adapted for repeated plastic bending by a user's hands to conform to a desired shape or contour of a patient's facial, oral cavity, or airway anatomy. The wire may be encased and is formed of a non-magnetic material. The wire may have sufficient strength to enable a user to insert the oral cannula through and past the oral cavity. At least one aperture of the gas delivery lumen may be located in a sidewall of the gas delivery lumen. The gas delivery lumen may have a sealed tip. The end-tidal $CO_2$ inlet may be distal relative to the gas diverter.

In some embodiments, a method of administering a treatment gas and sampling end-tidal $CO_2$ for a patient, includes a step of inserting an oral cannula to a patient's mouth. The oral cannula includes a treatment gas delivery lumen including at least one aperture near a distal end of the treatment gas delivery lumen; an end-tidal $CO_2$ sampling lumen. The cannula also includes a cap having (i) a gas diverter adapted for diverting at least a portion of the treatment gas and (ii) an end-tidal $CO_2$ inlet including flutes and apertures there between that are in communication with the end-tidal $CO_2$ sampling lumen. The oral cannula is adapted for custom bending or has a bend such that the oral cannula is insertable and retainable in a patient's mouth and functional for supplying a treatment gas and sampling gas exhaled by the patient.

In some embodiments, the method includes providing treatment gas through the treatment gas delivery lumen, through at least one aperture in the treatment gas delivery lumen, and via the gas diverter. The method may also include drawing end-tidal $CO_2$ through the end-tidal $CO_2$ inlet and through the end-tidal $CO_2$ sampling lumen. The oral cannula may also include a hydrophobic filter in the end-tidal $CO_2$ sampling lumen. Additionally, the oral cannula may include a filter housing located in the cap and housing the moisture hydrophobic filter. The filter housing may be rigid and provide radial rigidity to the cap. The gas diverter may be a skirt at a periphery of the proximal end of the cap, i.e. elements 426 and 474 as seen well in FIG. 13. The skirt may form a plenum into which at least one aperture in the treatment gas delivery lumen opens, and the filter housing may provide rigidity to the skirt to inhibit occlusion of at least one aperture in the gas delivery lumen. The skirt may be continuous about the cap. The cap may include a body and a funnel that is housed within the body, and the filter housing is mounted to the funnel. The cap may include an end-tidal $CO_2$ sampling channel between the end-tidal $CO_2$ inlets and the end-tidal $CO_2$ sampling lumen. The filter may be disposed in the end-tidal $CO_2$ sampling channel. The rigid filter housing may be adapted for resisting occlusion of the end-tidal $CO_2$ sampling lumen channel. The cap may include a sampling recess and a delivery recess on a proximal end thereof. The end-tidal $CO_2$ sampling lumen may be located in the sampling recess. The treatment gas delivery lumen may be located in the delivery recess. The cap may be cylindrical. The flutes may form the distal-most portion of the cap. The filter may be at a base of the flutes. The oral cannula my include a shaping wire that is adapted for repeated plastic bending by a user's hands to conform to a desired shape or contour of a patient's facial, oral cavity, or airway anatomy. The wire may be encased and formed of a non-magnetic material. The wire may have sufficient strength to enable a user to insert the oral cannula through and past the oral cavity. At least one aperture of the gas delivery lumen may be located in a sidewall of the gas delivery lumen, and the gas delivery lumen may have a sealed tip. The end-tidal $CO_2$ inlet may be distal relative to the gas diverter.

BRIEF DESCRIPTION OF THE FIGURES

FIG. 1B is an enlarged illustration of the oral cannula of FIG. 1A;

FIG. 3A is a longitudinal cross-sectional view of the oral cannula of FIG. 2A;

FIG. 3D is an enlarged view of a portion of the sidewall of the oral cannula of FIG. 2A;

FIG. 3E is cross sectional view taken through lines 3E-3E of FIG. 3D;

FIG. 4A is a perspective view of a co-sheath lumen oral cannula, with hidden structure shown in dotted lines;

FIG. 4B is a perspective view of a coaxial lumen oral cannula, with hidden structure shown in dotted lines;

FIG. 5A is a perspective view of a side-by-side oral cannula;

FIG. 5B is a cross sectional view of the oral cannula of FIG. 5A;

FIG. 6A is a perspective view of another embodiment side-by-side oral cannula;

FIG. 6B is a cross sectional view of the oral cannula of FIG. 6A;

FIG. 7A is a perspective view of another embodiment side-by-side oral cannula;

FIG. 7B is a cross sectional view of the oral cannula of FIG. 7A;

FIG. 9A is a cross sectional view of an oral cannula illustrating another embodiment of aperture configuration;

FIG. 9B is an enlarged view of a portion of the sidewall of the oral cannula of FIG. 9A;

FIG. 9C is cross sectional view taken through lines 9C-9C of FIG. 9B;

FIG. 14 is a cross section, orthogonal view of the oral cannula of FIG. 13, taken through lines 14-14 of FIG. 13;

DESCRIPTION OF PREFERRED EMBODIMENTS

Figure 1A:
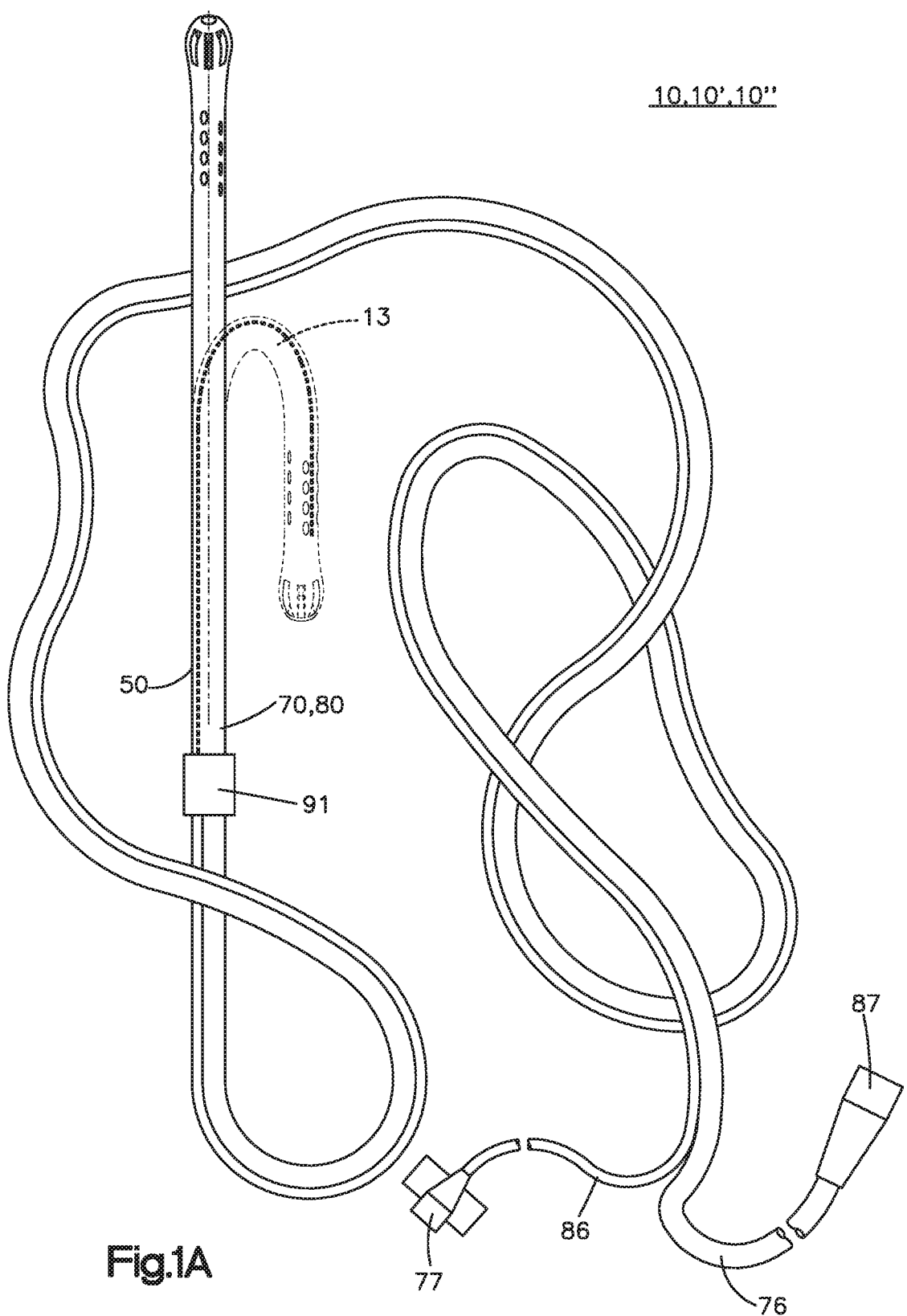
FIG. 1A is an illustration of an oral cannula and oxygen supply tubing and $ETCO_2$ sampling tubing.
Figures 2A, 2B:
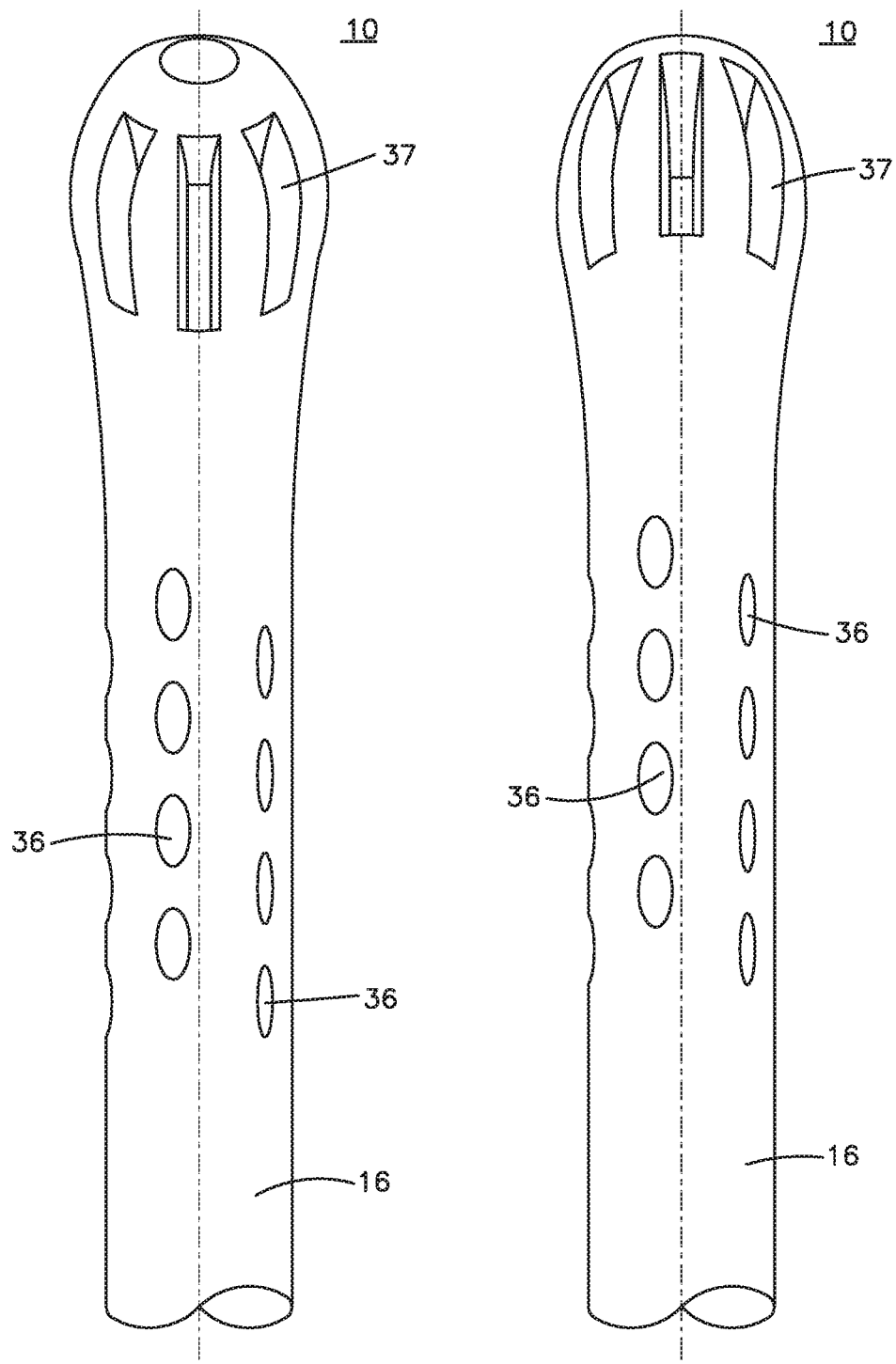
FIG. 2A is a perspective view of an oral cannula according to a first embodiment.
FIG. 2B is an opposite perspective view of the oral cannula of FIG. 2A.
Figure 3B:
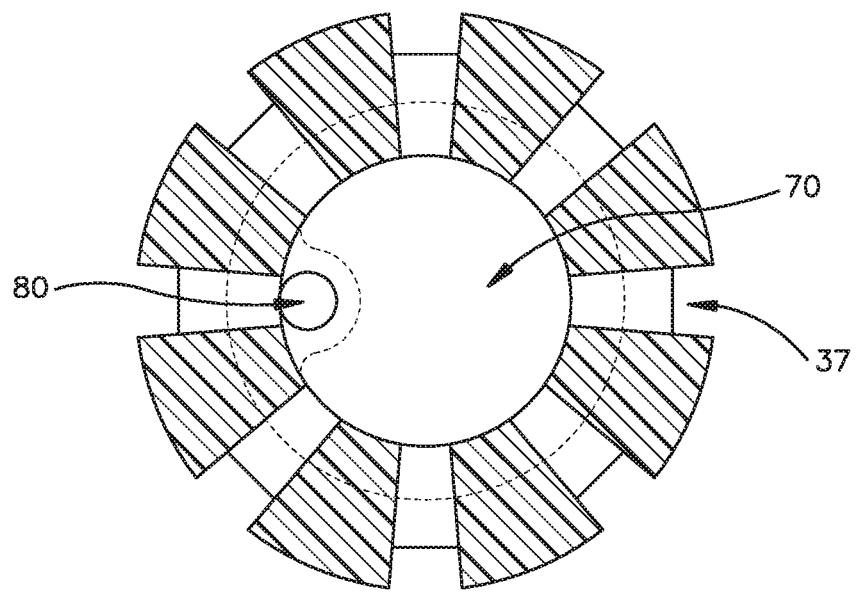
FIG. 3B is a transverse cross-sectional view taken through lines 3B-3B in FIG. 3A.
Figure 3C:
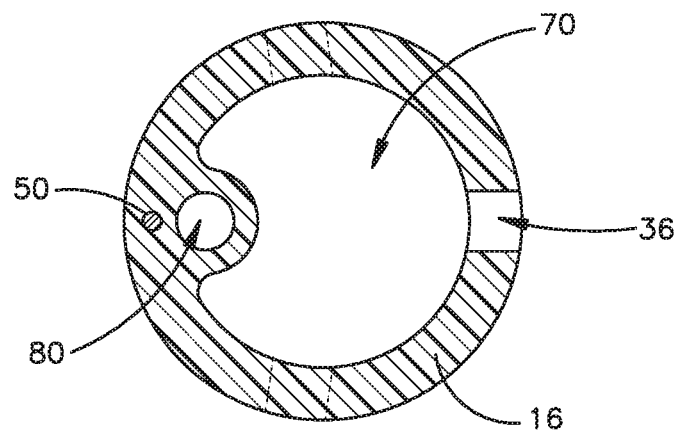
FIG. 3C is a transverse cross-sectional view taken through lines 3C-3C in FIG.

The oral cannula embodiments described below have a treatment gas delivery lumen and an end-tidal $CO_2$ sampling lumen. For convenience of illustration, the lumens are also referred to as an oxygen supply lumen and an end-tidal carbon dioxide ($ETCO_2$) lumen to reflect the most common treatment gas and the most common target for sampling the end-tidal $CO_2$. Each oral cannula is located or formed at the distal end of oxygen supply tubing and end-tidal carbon dioxide ($ETCO_2$) sampling tubing, which tubing is connected to a conventional capnography and oxygen supply and monitoring system at the end opposite the oral cannula. 430. Conventional Luer fittings may be used. Oxygen from the oxygen source (not shown in the figures) and controlled by the anesthetist or control system flows out through the oxygen supply lumen and exits through the oral cannula. Sampling gases are pulled through the oral cannula and the $ETCO_2$ sampling lumen to the capnography system FIGS. 1A and 1B illustrate an oral cannula that includes a first embodiment oral cannula 10, oxygen supply tubing 76, an end-tidal carbon dioxide ($ETCO_2$) sampling tubing 86, and (preferably) conventional fittings 77 and 87 on respective proximal ends of the tubing. Oral cannula 10 includes an oxygen supply tube lumen 70 and $ETCO_2$ sampling tube lumen 80. As shown in FIG. 1A, oxygen supply tube lumen 70 is at a distal portion of oxygen supply tubing 76; $ETCO_2$ sampling tube lumen 80 is at a distal portion of sampling tubing 86. In this regard, a portion of the tubing forms the oral cannula, and another portion of the tubing is extraneous to the oral cannula and extends from the oral cannula. A connector 91 is illustrated schematically to encompass any kind of connection or structure for connecting tubing 76, 86 to lumens 70, 80.

The oxygen supply tube 76 and the $ETCO_2$ sampling tube 86 (that is, the portions of the tubing that do not form the oral cannula 10) preferably are several feet long, affixed together in a side-by-side relationship, and terminate at conventional Luer fittings 77, 87 suitable for connection to an oxygen supply and $ETCO_2$ monitoring system Alternatively, tubing 76 and 86 may be configured in a co-sheath or coaxial configuration.

Tubing 76 and 86 preferably are formed of conventional materials, such as those used for conventional nasal cannula. Preferably, the tubing is conventional PVC. In an alternative embodiment, a plastic available from Saint-Gobain Performance Plastics Corporation under the TYGON® SE-200 and TYGON name may be used. This tubing has an inert liner and can be used as an $O_2$ delivery line. Tubing 76 and 86 are side-by-side tubes that are affixed together along their entire length, with (preferably) the supply lumen being larger in diameter than the sampling lumen. Other embodiments of the oral cannula described below may have coaxial or other tubing configurations, but the function and materials of the supply and sampling tubing is the same for all embodiments. In this specification, the term "tubing" refers to conventional, flexible tubing (described more fully below); the term "lumen" refers to the structure or the passage formed by the structure of the inventive oral cannula.

As best shown in FIGS. 2A, 2B, and 3A through 3E, oxygen supply lumen 70 and $ETCO_2$ sampling lumen 80 in the first embodiment are in a co-sheath configuration in which $ETCO_2$ sampling lumen 80 is enclosed within oxygen supply lumen 70 to form a portion of oral cannula body 16. In this regard, the term "co-sheath" as used in this description refers to a structure in which one tube is contained within another, even if the axes of the tubes do not fall on the same line, including when inner tube is attached to an inner wall of the outer tube. The term "coaxial" as used in this description refers to a structure in which tubes are oriented such that the longitudinal axes generally align, including when an inner tube is loose within the outer tube. A coaxial configuration is a subset of a co-sheath configuration.

Figure 10A:
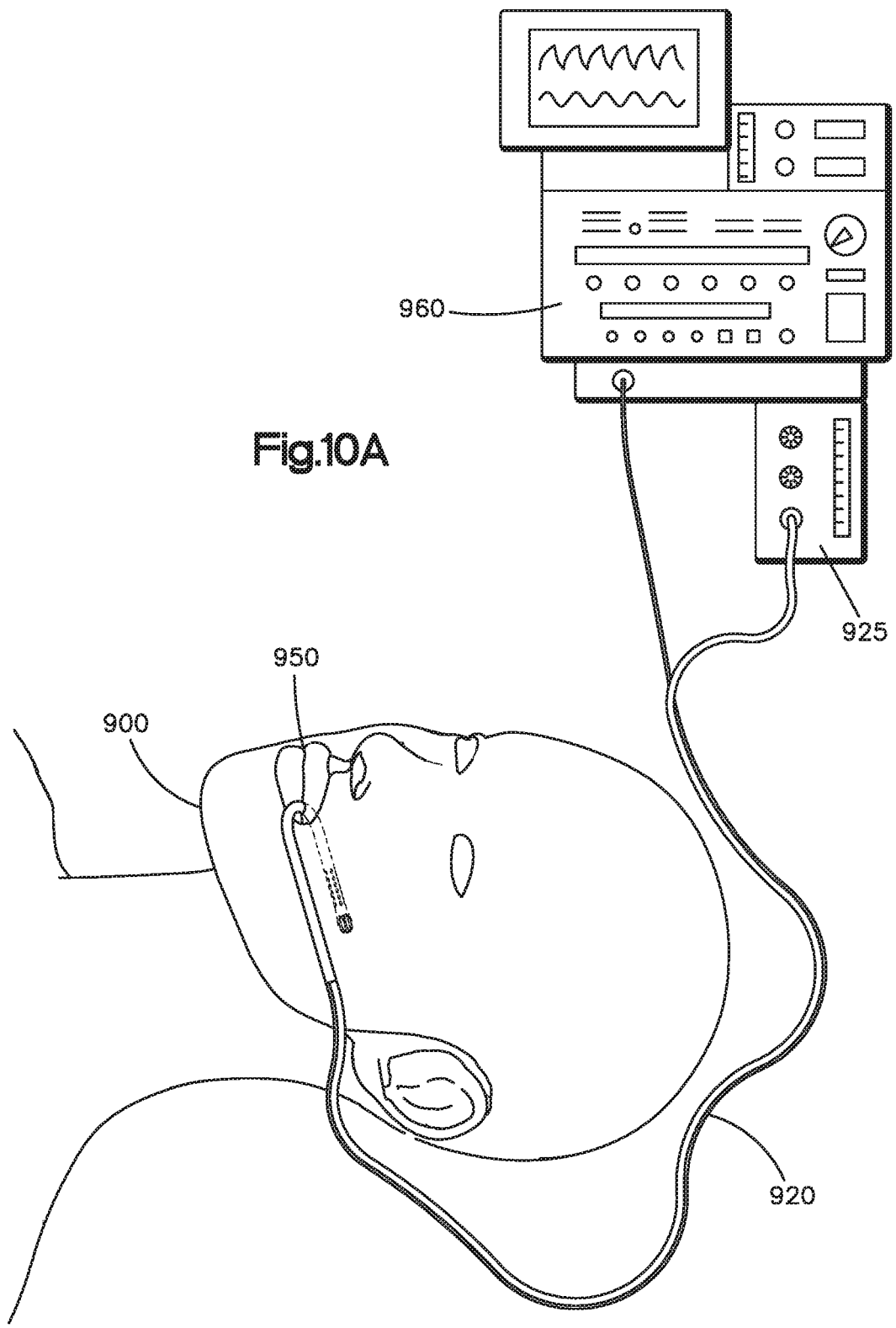
FIG. 10A is a schematic view of an oxygen supply and capnography system employing the present invention.
Figure 10B:
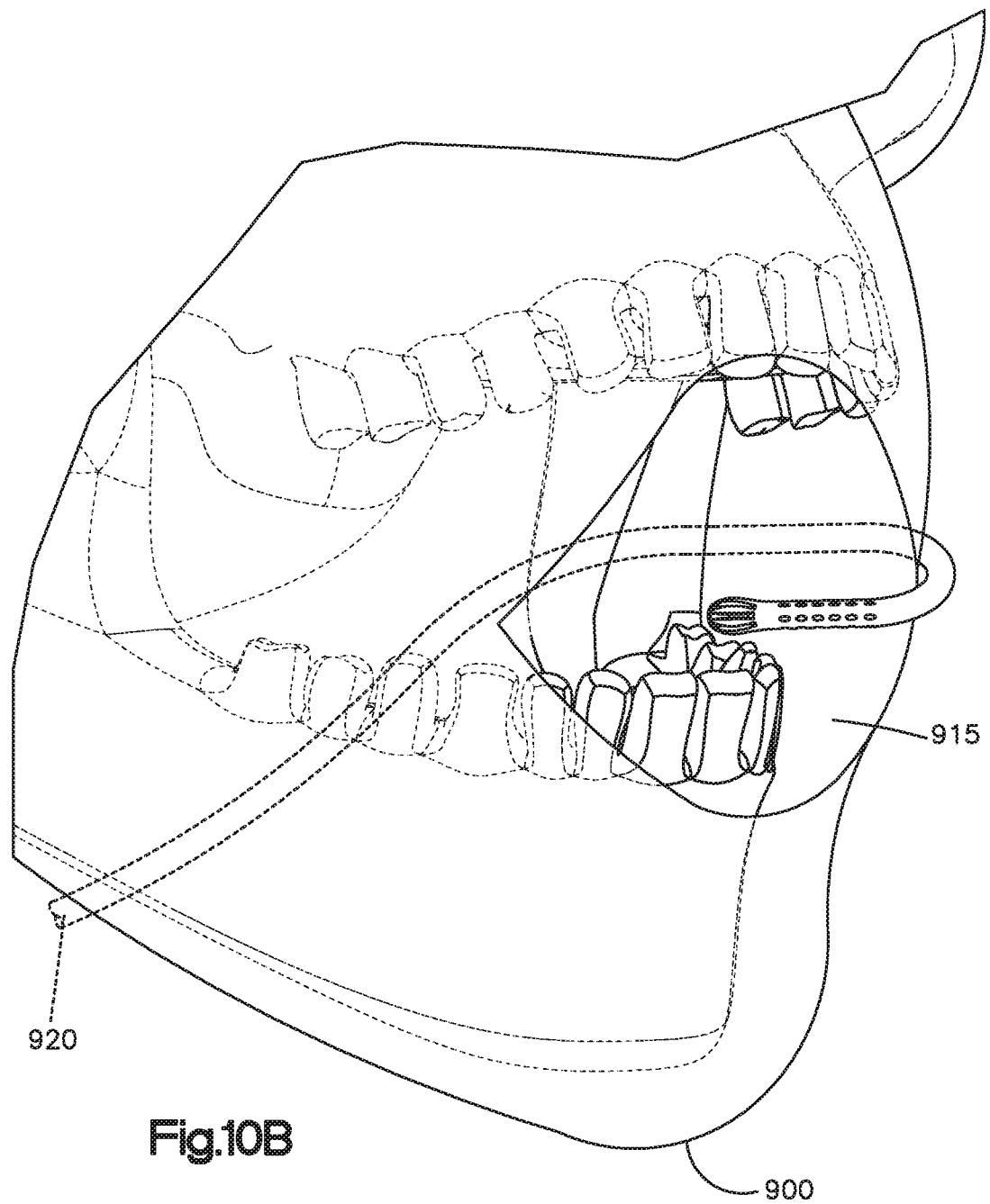
FIG. 10B is an enlarged schematic view of an oral cannula residing in a patient's mouth.

Body 16 may be integrally formed with the tubing, or body 16 may be a unitary (that is, stand-alone) piece that has openings into which oxygen supply tubing 76 and $ETCO_2$ sampling tubing 86 fit and are attached (including by a separate connector 91 to mate the parts). The sidewall of body 16 includes plural apertures 36 that are in communication with the interior of lumen 70 and tubing 76 such that oxygen supplied by the oxygen source (illustrated in FIG. 10A) and controlled by the anesthetist or control system flows out of oral cannula 10 through apertures 36. Body 16 also includes apertures 37, 38 that are in fluid communication with plenum 74, sampling lumen 80, and tubing 86, such that sampling can be controlled by the $ETCO_2$ monitoring system In this regard, a distal end of oxygen supply lumen 70 is sealed by a bulkhead 72 such that a distal end of the oral cannula distal to the bulkhead forms a plenum 74, as best shown in FIG. 3A. The portion of the oral cannula including the bulkhead and plenum can be referred to as a tip, such as a cap, for example, a bulb. In this regard, the term "tip" in this disclosure is used broadly to refer to any end structure. The tips may be formed of rigid plastic sleeve. Alternatively, the tips may be formed of a soft plastic.

FIG. 3D is an enlarged view of a portion of the sidewall of the oxygen supply lumen 70 illustrating a configuration of apertures 36. In this regard, apertures 36 define a centerline that forms an angle A from a longitudinal centerline, which is horizontal as oriented in FIGS. 3D and 3E. Preferably, angle A is between 25 and 75 degrees, more preferably between 40 and 60 degrees, and most preferably between 45 and 50 degrees. Further, a distal or upper portion of apertures 36 include a scoop 92 intended to inhibit unintentional blocking of the apertures by contact with a patient's tissues.

FIGS. 9A, 9B, and 9C illustrates an oral cannula 910 having apertures 936 that are oriented perpendicular to the sidewall. Apertures 936 includes a scoop at the distal end, which are intended to inhibit unintentional blocking of the apertures by contact with a patient's tissues. Scoops 92 and 992 are optional, as the present invention encompasses straight holes without scoops.

FIGS. 4A and 4B illustrate additional configurations of co-sheathed oral cannula. FIG. 4A illustrates oral cannula 10' having a bulkhead 72' that is a barrier that seals the end of supply lumen 70. Sampling lumen 80 protrudes through bulkhead 72' such that plenum 74 is connected to sampling lumen 80 and not in communication with supply lumen 70. FIG. 4B illustrates co-axial oral cannula 10" having a bulkhead 72", which functions the same as bulkhead 72'. Sampling lumen 80 protrudes through bulkhead 72" at or near the centerline of lumen 70.

Each bulkhead 72, 72', and 72" defines the corresponding plenum 74, 74', and 74." The text below will employ the reference numerals 72 and 74 to refer to any embodiment of the bulkhead and plenum for ease of description, and reference numeral 10 to refer to any of the embodiment in FIGS. 2A through 4B. Apertures 37 are formed in the plenum wall around the body of the plenum 74. An end aperture 38 may be formed at the distal-most end of oral cannula 10.

Oxygen from oxygen supply tubing 76 flows within supply lumen 70 on the outside of sampling lumen 80 to exit from apertures 36. Because bulkhead 72 forms the end of supply lumen 70, oxygen does not enter plenum 74. Rather, gas is pulled into plenum 74 through apertures 37 and 38 and through sampling lumen 80 by the action of the suction from the $ETCO_2$ sampling system.

Body 16, as illustrated in FIG. 1B, has a bend 13 that may be (optionally) formed by a wire 50 or may be formed upon molding body 16, as explained more fully below. Body 16 can be formed of a rigid plastic or from a soft plastic, according to the particular design parameters of the oral cannula.

Figure 8A:
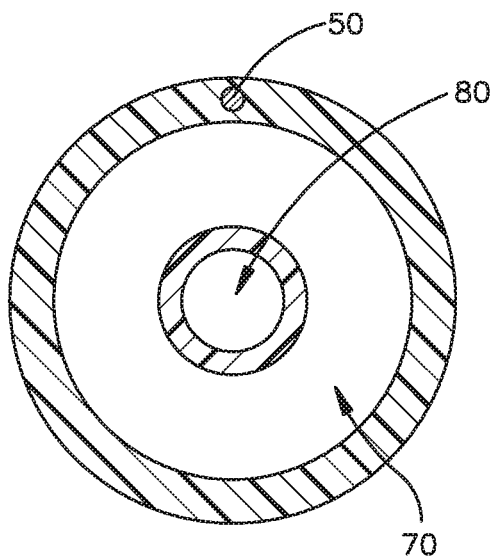
FIG. 8A is an enlarged cross-sectional view of coaxial lumens of an oral cannula.
Figure 8B:
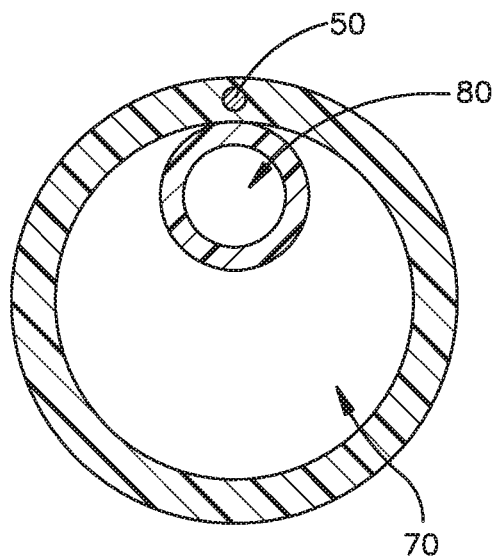
FIG. 8B is an enlarged cross-sectional view of co-sheath lumens of an oral cannula.
Figure 8C:
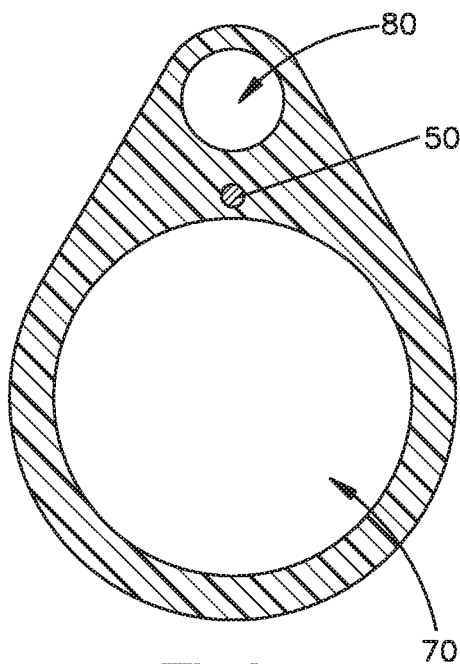
FIG. 8C is an enlarged cross-sectional view of another configuration of co-sheath lumens of an oral cannula.
Figure 8D:
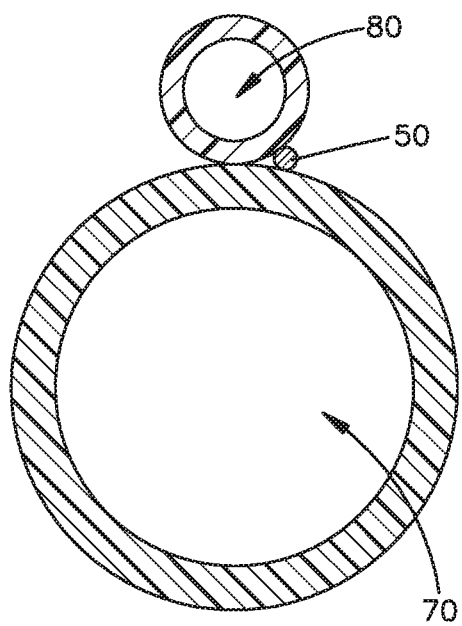
FIG. 8D is an enlarged cross-sectional view of side-by-side lumens of an oral cannula.

FIG. 8A illustrates a common coaxial configuration in which the axes are or can lie literally on the same axis. The configuration of FIG. 8B is, in the nomenclature of this specification, also coaxial if the tube of lumen 80 is not attached to the tube of lumen 70, as the loose lumens will sometimes be coaxial. If the outside of lumen 70 is adhered to the inside of lumen 80 in FIG. 8, then the lumens have a co-sheath configuration. FIG. 8C illustrates another co-sheath configuration in which the outer sheath does not have a circulate cross section. FIG. 8D illustrates an oral cannula having a side-by-side (that is, not a co-sheath configuration).

FIGS. 5A and 5B illustrate an alternative embodiment oral cannula 110 including a tip 112, such as a cap. Tip 112 is formed by an elongate, supply body 116, such as a cylindrical or nearly cylindrical supply body, that forms an oxygen supply lumen 170 and a cylindrical, or nearly cylindrical sampling body 118 that forms an $ETCO_2$ sampling lumen 180. Bodies 116 and 118 preferably are unitary (that is, formed of a single piece of plastic and are not detachable from one another) and side-by-side. Preferably, tip 112 is approximately 1.0 to 3.0 inches long, preferably at least 1.5 inches long, and optionally includes a bend (not shown in FIGS. SA and 5B), to house the entirety of the oxygen supply lumen and $ETCO_2$ sampling lumens of the oral cannula. In this alternative, the tip would be connected to tubing 76 and 86, and the tip may be formed of a pre-bent rigid plastic, a pre-bent soft plastic, or be supplied with a shaping wire 50.

Oxygen supply lumen 170 has a proximal end 132 and a distal end 172. An opening 134 at proximal end 132 is sized to receive oxygen supply tubing 76. Tubing 76 is inserted into opening 134 and preferably is adhered or welded by conventional means. The sidewall of the body 116 includes plural openings 134 that are in communication with the interior of lumen 170 and tubing 76 such that oxygen supplied by the oxygen source (not shown in Figure) and controlled by the anesthetist or control system flows out of oral cannula 10 through apertures 136. In this regard, the distal end 172 terminates at a barrier and is sealed such that no oxygen flows out of the distal end of the oral cannula parallel to the longitudinal axis of oral cannula 110 or into plenum 174 (explained below).

$ETCO_2$ lumen 180 has a proximal end 142 and a distal end 148. An opening 144 at proximal end 142 is sized to receive $ETCO_2$ sampling tube lumen 180. Lumen 180 is inserted into opening 144 and preferably is adhered or welded together by conventional means. The sidewall of the body 118 preferably has no apertures that open into sampling lumen 180. Rather, sampling body 118 distally extends past the distal end of the oxygen supply lumen 170 into a plenum 174. Sampling body 118 at plenum 174 has apertures 137 and (optionally) apertures on the distal end 139 of oral cannula 110 (not shown in FIG. 5). Apertures 137 preferably are distributed around the circumference or periphery of plenum 174 such that sampling apertures 137 are distal to all of oxygen supply apertures 136. Apertures 137 enable communication and flow through or near the end of body 118 into the interior of sampling lumen 180 and sampling tubing 86 when pulled by the ETCO$_2$ monitoring system (not shown in the figures). Distal end 139 defines the distal end of oral cannula 110.

FIGS. 6A and 6B illustrate another side-by-side embodiment oral cannula 210 including a tip 212, an oxygen supply lumen 230, and an ETCO$_2$ sampling lumen 240. Tip 212 is formed by a nearly cylindrical supply body 216 that forms a portion of oxygen supply lumen 230 and a cylindrical sampling body 218 that forms a portion of ETCO$_2$ sampling lumen 240. Bodies 216 and 218 are unitary (that is, formed of a single piece of plastic and are not mutually detachable from one another) and side-by-side. Preferably, tip 212 is between 0.5 inches and 1.5 inches long (measured parallel to the longitudinal axis). In cross section or in an end view, lumens 230 and 240 form a figure eight.

In this regard, oxygen supply lumen 230 of the oral cannula 210 can be formed in part by tip 212 and oxygen supply lumen 270 (that is, a portion of tubing 76). The ETCO$_2$ sampling lumen 240 of oral cannula 210 can be formed in part by tip 212 and sampling lumen 280 (that is, a portion of tubing 86). In other words, a portion of tubing 76 and 86 can form a portion of oral cannula 210. And a portion of tip 212 can form a portion of oral cannula 210. Alternatively, embodiment oral cannula 210 encompasses an oxygen supply lumen 230 that is short and/or includes only a fitting to close off the end of tubing. In the embodiment shown in FIGS. 6A and 6B, body 216 includes an opening recess 234 sized to receive oxygen supply tube lumen 270, which is inserted into the opening recess 234 and preferably is adhered or welded by conventional means. The sidewall of the tubing that forms supply lumen 270 includes plural apertures 236 that are in communication with the interior of lumen 270 and tubing 76 such that oxygen supplied by the oxygen source and controlled by the anesthetist or control system flows out of oral cannula 210 through apertures 236. In this regard, the distal end of the supply lumen 270 is sealed by body 216 at a seal 272.

ETCO$_2$ lumen 240 of tip 212 has an opening 244 at proximal end 242 that is sized to receive ETCO$_2$ sampling tube lumen 280. Lumen 280 is inserted into opening 244 and preferably is adhered or welded together by conventional means. Sampling body 218 distally extends past the distal end of the oxygen supply lumen 270 to form a plenum 274. Sampling body 218 has apertures 237 near its distal end 239 and (optionally) apertures on its distal end (not shown in FIG. 6). Apertures 237 preferably are distributed around the circumference or periphery of plenum 274 and the sampling apertures 237 are distal to all of oxygen supply apertures 236. Apertures 237 enable communication and flow through or near the end of body 218, in some circumstances making a right turn, into the interior of sampling lumen 240 and sampling tubing 86 when pulled by the ETCO$_2$ monitoring system. Distal end 239 defines the distal end of oral cannula 210.

FIGS. 7A and 7B illustrate another side-by-side embodiment oral cannula 310 that includes a tip 312, such as a cap, for example a bulb, that may be formed of a unitary piece having openings into which oxygen supply tubing and ETCO$_2$ sampling tubing fit and are attached or may formed integral with tubing 76 and 86.

Oral cannula 310 encompasses an oxygen supply lumen 330, an ETCO$_2$ sampling lumen 340, a barrier 372, and a plenum 374. Tip 312 includes a port 346 that extends through the sidewall of a tip 312 on the distal side barrier 372 to communicate with plenum 374. Tip 312 forms plenum 374 and includes sampling apertures 337 and end aperture 338.

The sidewall of the lumen 330 includes plural apertures 336 that are in communication with the interior of supply lumen 330 to enable oxygen to flow out of oral cannula 310. Oxygen supply lumen 330 terminates at barrier 372. Sampling lumen 340 extends exterior of the supply lumen 330, through port 346. Alternatively (not shown), port 346 can be located on the proximal side of barrier 372 such that port 346 extends through supply lumen 330 to pierce barrier 372 in a configuration like that described for embodiments having a bulkhead. In another alternative (not shown), sampling lumen 340 may extend all the way through supply lumen 330 and terminate only in an aperture at the distal-most end portion of the oral cannula. The latter alternative does not require a bulkhead. Plenum apertures 337 and 338 enable gas to be drawn through apertures 337 and 338, plenum 374, port 346, sampling lumen 340, and into sampling tubing 86 (not shown in FIGS. 7A and 7B).

Oral cannula 310 may be pre-formed with a bend. Tip 312 can be formed of a rigid plastic or from a soft plastic, according to the particular design parameters of the oral cannula and in embodiments in which tip 312 is elongated (not shown), may include a bend, as described elsewhere in this disclosure. Tip 312 can be formed as a separate structure that is fused to lumens 330 and 340, formed integral with lumen 330 by closing its distal end, or by other means as understood by persons familiar with tubing technology.

For the side-by-side embodiments of FIGS. SA through 7B, the oxygen supply tube 76 and the ETCO$_2$ sampling tube 86 (that is, the portions of the tubing that do not form the oral cannula 110, 210, 310) preferably are several feet long, affixed together in a side-by-side relationship, and terminate at conventional Luer fittings 77, 87 suitable for connection to an oxygen supply and ETCO$_2$ monitoring system Alternatively, tubing 76 and 86 may be configured in a coaxial configuration.

Tubing 76 and 86 preferably are formed of conventional materials, such as those used for conventional nasal cannula. Preferably, tubing 76 and 86 are conventional PVC, as will be understood by persons familiar with medical devices in this field. This tubing has an inert liner and can be used as an O$_2$ delivery line. Tubing 76 and 86 are side-by-side tubes that are affixed together along their entire length, with (preferably) the supply lumen being larger in diameter than the sampling lumen. Other embodiments of the oral cannula described below may have coaxial or other tubing configurations, but the function and materials of the supply and sampling tubing is the same for all embodiments. In this specification, the term "tubing" refers to conventional, flexible tubing (described more fully below); the term "lumen" refers to the structure or the passage formed by the structure of the inventive oral cannula.

Referring to FIGS. 11 through 15B to illustrate a preferred embodiment, an oral cannula assembly 400 includes treatment gas delivery tubing 76, end-tidal CO$_2$ sampling tubing 86, (preferably) conventional fittings 77 and 87 on respective proximal ends of the tubing, and an oral cannula 410. Oral cannula 410 is referred to as an intraoral cannula, as a subset of an oral cannula, to refer to diverse positioning within the oral space throughout the oral cavity and beyond, including positioning the tip near or in contact with the oropharynx.

The oxygen supply tube 76 and the ETCO$_2$ sampling tube 86 (that is, the portions of the tubing that do not form the oral cannula 410) preferably are several feet long, affixed together in a side-by-side relationship, and terminate at conventional Luer fittings 77, 87 suitable for connection to an oxygen supply and ETCO$_2$ monitoring system 925, 960.

Alternatively, tubing 76 and 86 may be configured in a co-sheath or coaxial configuration.

Figure 11:
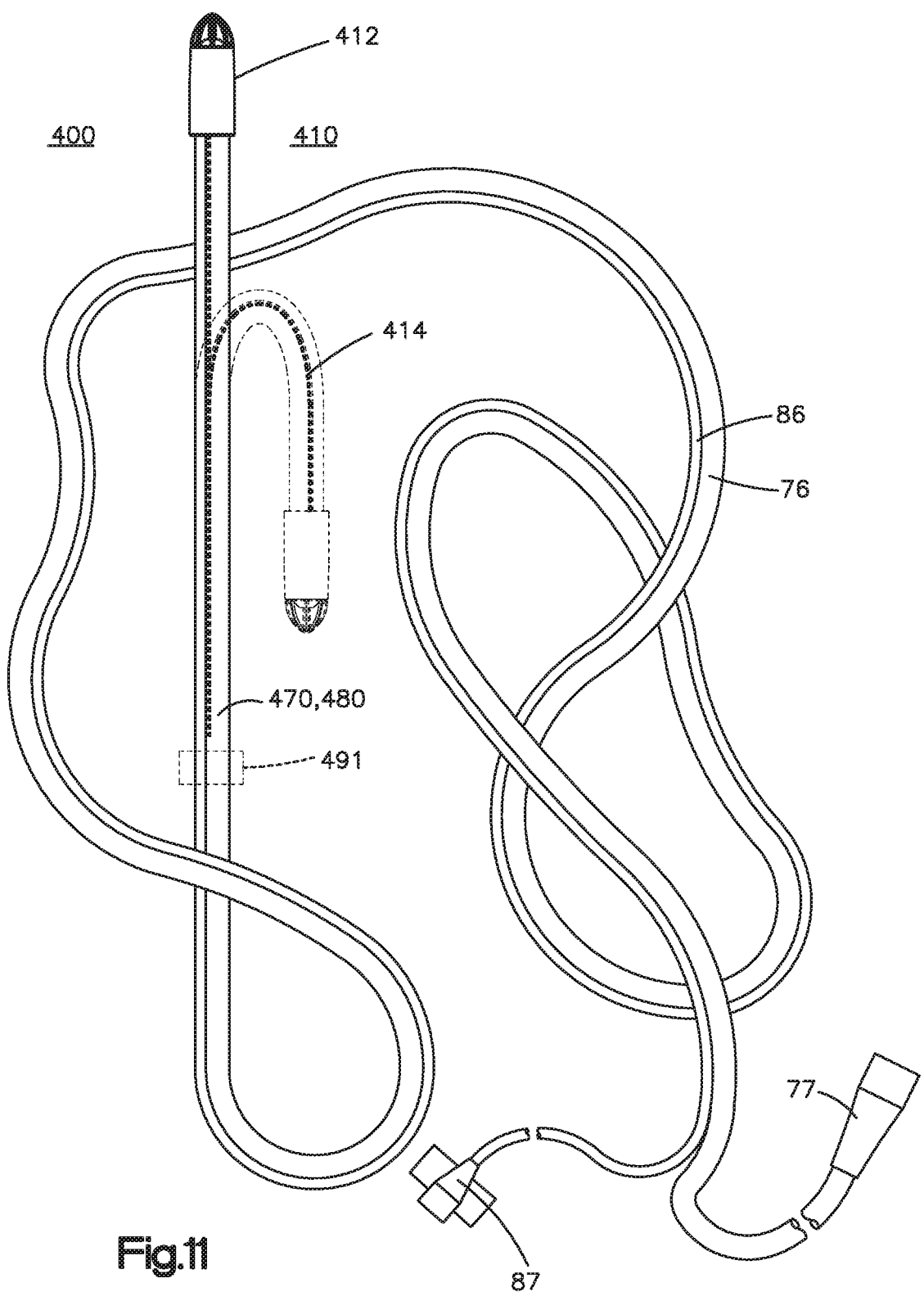
FIG. 11 is an illustration of an oral cannula assembly and treatment gas delivery lumen and end-tidal $CO_2$ sampling lumen.
Figure 12:
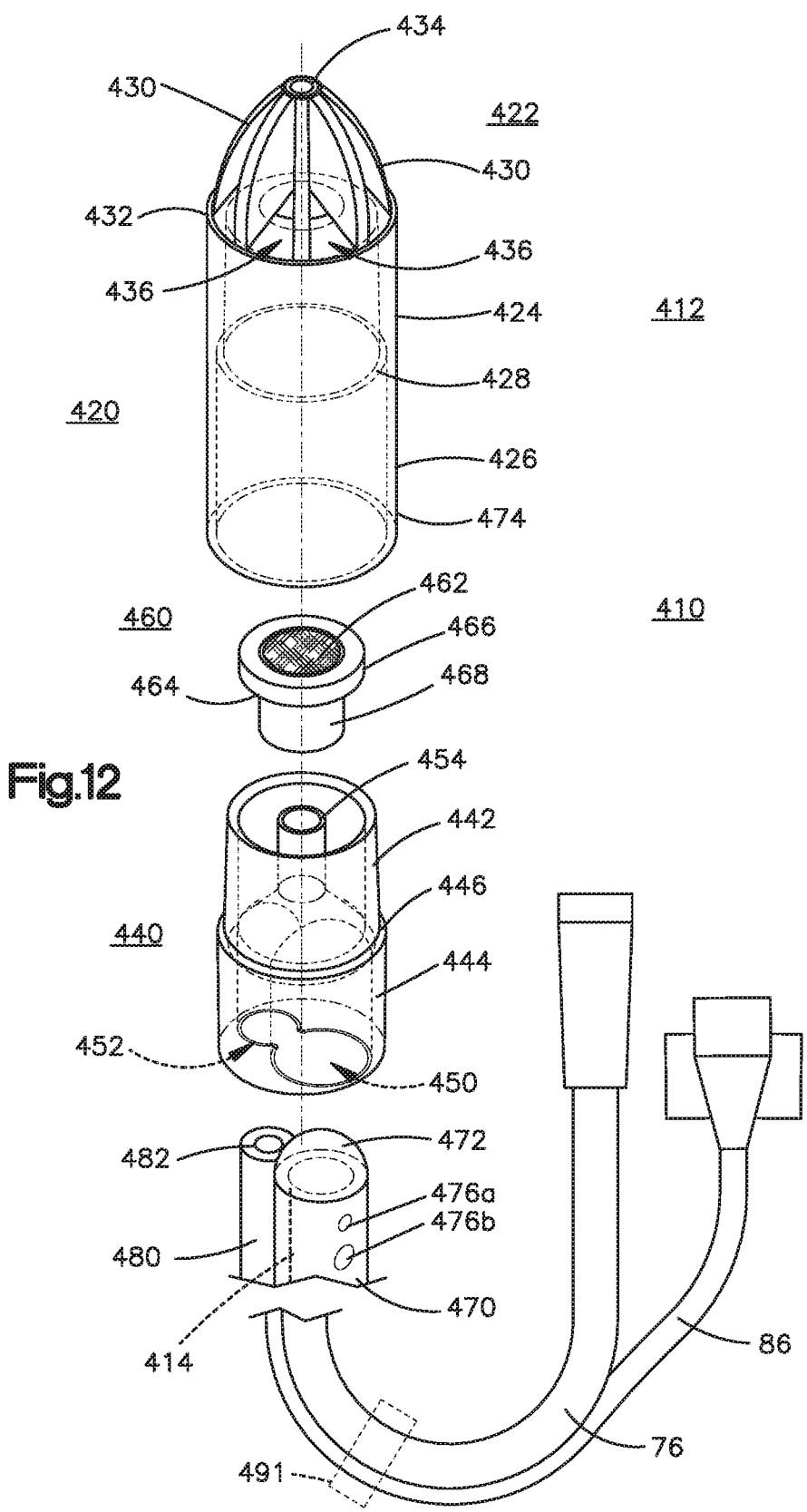
FIG. 12 is an enlarged, perspective exploded view of the oral cannula of FIG. 11.
Figure 13:
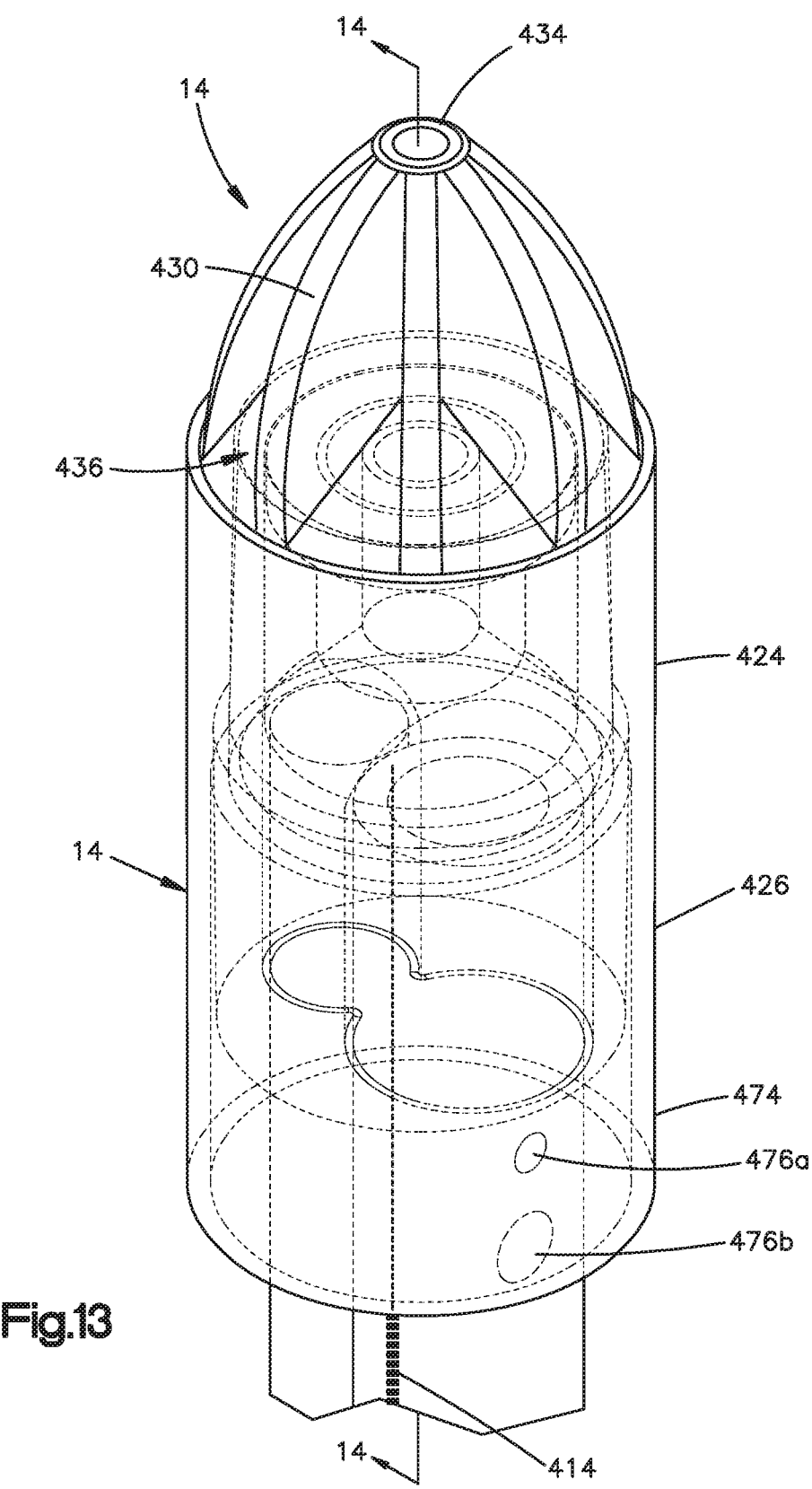
FIG. 13 is an enlarged, perspective view of a portion of the oral cannula, including the cap assembly internal parts shown in relief.
Figure 15A:
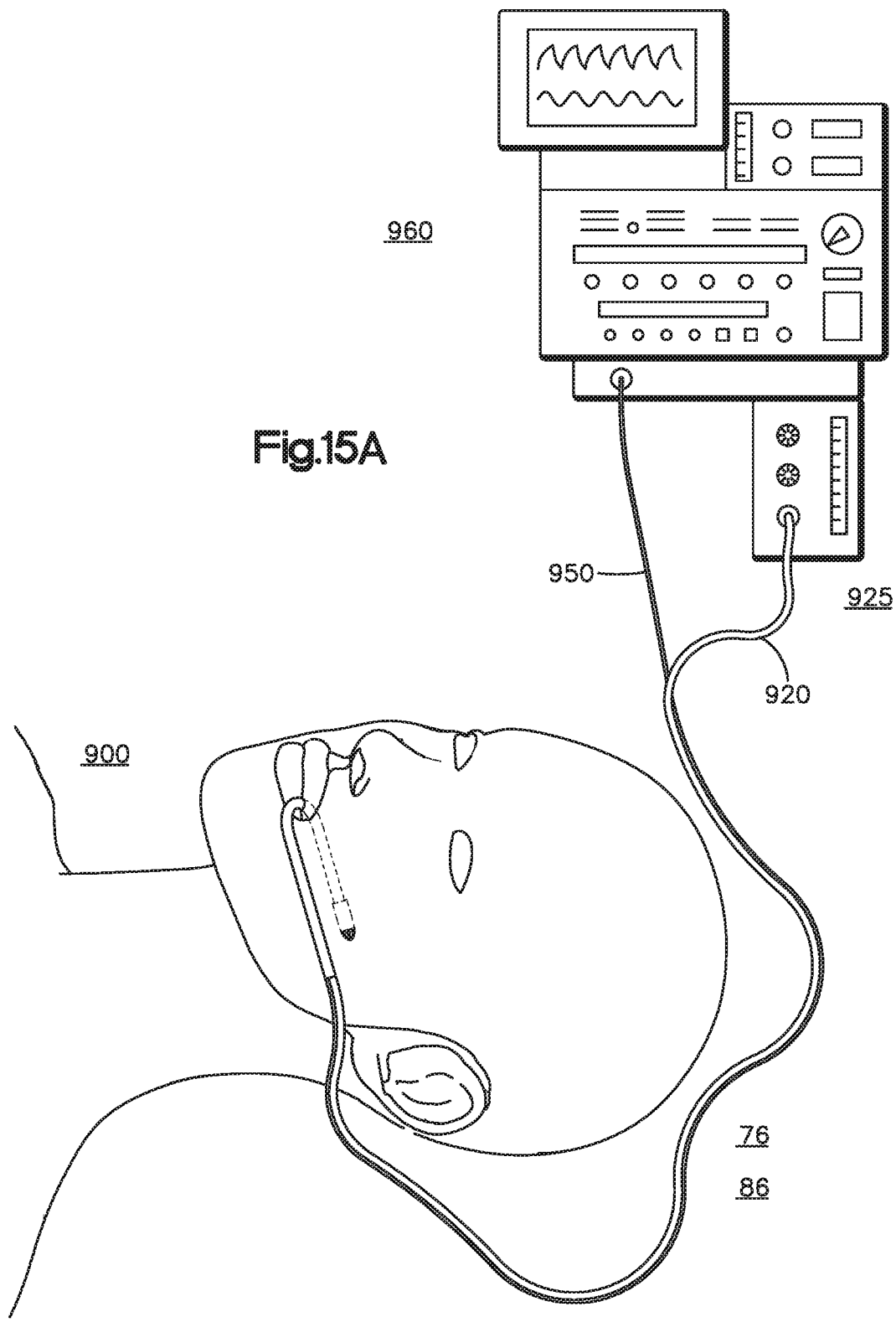
FIG. 15A is a schematic view of an oxygen supply and capnography system employing the present invention.
Figure 15B:
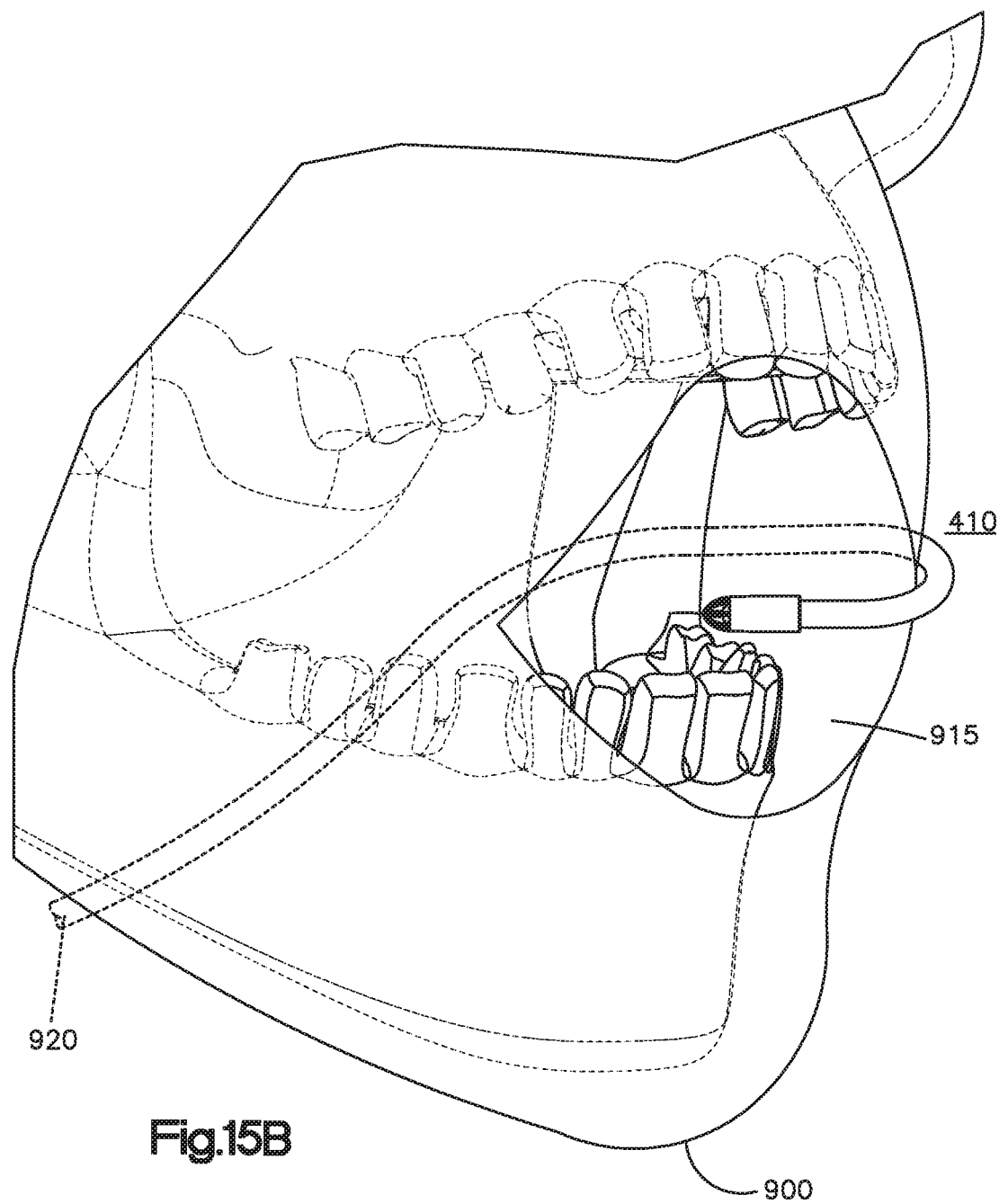
FIG. 15B is an enlarged schematic view of a flexible intraoral cannula residing in a patient's mouth.

Oral cannula 410 includes a treatment gas delivery lumen 470, an end-tidal $CO_2$ sampling lumen 480, a cap assembly 412, and a shaping wire 414. As shown in FIG. 12, delivery lumen 470 is at a distal portion of tubing 76; sampling lumen 480 is at a distal portion of sampling tubing 86. In this regard, a portion of the tubing forms the oral cannula, and another portion of the tubing is extraneous to the oral cannula and extends from the oral cannula. A connector 491 is illustrated schematically to represent any kind of connection or structure for connecting tubing 76, 86 to lumens 470, 480. As shown in FIGS. 11, oral cannula assembly 400 has no connector between tubing 76 and 86, as portions on the oral cannula are formed on the distal portions of the tubing.

Cap assembly 412 includes an outer cap body 420, a cap insert 440, and a filter assembly 460. Outer cap body 420 includes a flute portion 422 at its distal most region, a cylindrical middle sleeve 424, and a cylindrical proximal sleeve 426, which includes a skirt 474. Flute portion 422 includes plural flutes 430 that are radially oriented gussets or webs that extend from cap middle sleeve 424 at a flute base 432 to a distal tip 434. Preferably, flutes are joined together at the longitudinal centerline for mutual support. Flutes 430 in the embodiment shown in the figures are tapered to narrow in the direction of tip 434. Other configurations of flutes are contemplated. The spaces between adjacent flutes 430 form apertures 436.

Cap middle sleeve 424 and cap proximal sleeve 426 are cylindrical and have the same outer diameter. Cap proximal sleeve 426 extends downwardly or proximally from the lower or proximal end of middle portion 424. Proximal sleeve 426 has a greater internal diameter than the internal diameter of middle portion 424 and thus defines a frusto-conical shoulder 428 at the juncture of the inboard surfaces of portions 424 and 426.

Cap insert 440 includes a cylindrical upper or distal body 442, a cylindrical lower or proximal body 444, and a frusto-conical shoulder 446 between bodies 442 and 444. The outer diameter of distal body 442 is greater than that of proximal body 444 such that the outboard surface of cap insert 440 forms an upwardly oriented funnel shape. The outer diameter of distal body 442 matches the inner diameter of middle sleeve 424 of the outer cap body 420. The outer diameter of proximal body 444 matches the inner diameter of proximal sleeve 426 of the outer cap body 420.

The lower or proximal end of proximal body 444 has a recess 450 for receiving delivery lumen 470 and a recess 452 for receiving sampling lumen 480. A gas channel 454 extends from the uppermost rim of cap insert 440 and is in fluid communication with sampling recess 452. In this regard, channel 454 preferably is concentric with distal body 442 throughout all or most of distal body 442 and bends or angles to be deviate from the longitudinal centerline at the proximal end of proximal body 444. Sampling recess 452 is thus in communication with channel 454. Delivery recess 450 is shown as opening into sampling recess 452, as delivery lumen 470 has a sealed tip 472, as explained below. Alternatively, delivery recess 450 may be sealed (not shown in the Figures).

Filter assembly 460 includes a hydrophobic filter element 462 and a filter housing 464. Filter housing includes a circular flange 466, and a downwardly depending skirt 468. Hydrophobic filter element 462 is located on or radially within flange 466. The hydrophobic filter element 462 is such that it prevents saliva and mucus from being drawn into the channel, such as channel 454, and/or otherwise blocking or impeding the desired flow of sample gas. Preferably, filter housing 464 is rigid to provide radial rigidity to cap assembly 412.

Shaping wire 414 preferably is generally as described herein for other embodiments, and has the attributes of being able to be bent by the hands of the user, retaining a bend applied by a user upon insertion into a patient's mouth, and preferably being sufficiently rigid to enable the user to insert it into the airway of the patient (past the oral cavity and in some circumstances into the oropharynx and beyond) if needed. The inventors have found that a 16 gauge, medical grade copper wire is sufficient for this purpose. Wires of similar gauge having the same or higher yield strength may be used. Wires (and other structures) of other materials and yield strength and/or resistance to bending moments may be employed if having the same or greater bending stiffness than a 16 gauge, medical grade copper wire. Preferably, wire 414 is encased or encapsulated within the material of lumen 470 and/or 480.

Delivery lumen 470 is a conventional tube material having a fused or blocked terminal end 472 and apertures, preferably a pair of round apertures 476a and 476b in the sidewall of delivery lumen 470. Preferably, upper or distal aperture 476a has a smaller diameter (or for apertures that are not round, a smaller cross-sectional area) than that of lower or proximal aperture 476b to encourage even or balanced airflow through the two apertures. The location of apertures 476a and 476b depends on the dimensions of skirt 474, as explained below. Sampling lumen 480 preferably is a continuous, unbroken tube of conventional material described above that is open at its terminal proximal end 482.

Referring particularly to FIGS. 11 through 14 to described the assembled device, filter assembly 460 is located on cap insert 440 such that circular flange 466 is in contact with a proximal rim of cap insert distal body 442, an outboard surface of filter skirt 468 is in contact with or within the inboard surface of distal portion 442 of insert body 440, and an outboard surface of insert channel 454 is in contact with or within an inboard surface of filter skirt 468. Thus, sampling tubing 86 is in fluid communication with the underside of filter element 462 via sampling lumen 480, sampling recess 452, and insert channel 454.

As best shown in FIG. 14, cap insert 440 is located within cap outer body 420 such that the outboard surface of distal body 442 is in contact with or within the inboard surface of middle sleeve 424 of outer cap body 420, the outboard surface of proximal body 444 is in contact with or within the inboard surface of proximal sleeve 426, and shoulder 446 is in contact with shoulder 428. In this regard, cap insert 440 may be glued or otherwise affixed to cap outer body 420, held together in a press fit or interference fit, or have any other fixed relationship. Preferably, outer body 420 and insert body 440 are formed of flexible material similar to that of the PVC tubing material described above. Flutes 430 are formed of a firm, pliable plastic, such as a conventional plastic suitable for thermoforming or injection molding, such that the flutes resist deformation in the patient's mouth to prevent or inhibit occlusion.

Outer cap proximal sleeve 426 extends below or proximal to proximal body 444 of insert 452 to form a skirt 474. Skirt 474 is radially spaced apart from treatment gas delivery lumen 470 and end-tidal $CO_2$ sampling lumen 480 to form a plenum 478 about the inner circumference of the inboard surface of skirt 474. In this regard, apertures 476 are located in or open into plenum 478, or in other words are located distally or above the proximal or lower end of skirt 474.

Preferably, skirt 474 is a continuous circle, but other configurations (not shown) by which skirt 474 protects or covers apertures 476 from being occluded are contemplated.

In operation, a user bends oral cannula 410 to a desired configuration, based on the user's oral cavity shape and size and like parameters of the application. Oxygen or other treatment gas is delivered through lumen 76 and into lumen 470. As lumen 470 is blocked at its distal end 472, the flow of treatment gas turns 90 degrees to exit through apertures 476a and 476b into plenum 478. Plenum 478 may enhance diffusion circumferentially around lumens 470 and 480. The treatment gas flow turns again 90 degrees to exit below skirt 474, as illustrated by the arrows in FIG. 14. $ETCO_2$ is drawn through apertures 436 between flutes 430, through filter element 462, through channel 454, through lumen end 482 and into $ETCO_2$ sampling lumen 480.

The oral cannula described herein can be molded with a bend that resists deformation, may be molded with a bend that is plastically deformable such that the shape of the oral cannula can be adjusted as desired by the anesthetist or other users, may be formed with a shaping wire encapsulated in the plastic, may be formed with a shaping wire exterior to and adhered or mechanically affixed to the body of the cannula, optionally with the wire protected by a protective sheath, or may include other mechanical support (as will be understood by persons familiar with deformable plastic medical devices). In embodiments in which the oral cannula is intended to be deformable, the oral cannula is intended to be deformed by a user's hands. In embodiments in which the oral cannula is intended to be rigid, the oral cannula is stiff enough to resist deformation by the force of a user's hands.

For any of the embodiments in which the oxygen supply lumen and $ETCO_2$ sampling lumen are not fixed in a concentric, coaxial configuration and which have a bend, it is preferred that the sampling lumen be near the inside radius of the bend to enhance the area of the oxygen supply lumen wall that is available for oxygen supply apertures.

As illustrated schematically in FIGS. 10A and 10B and 15A and 15B, a patient 900 can have an oral cannula 10, which reference numeral is intended to represent any configuration herein (including oral cannula 410), which is shaped and placed in his mouth 915. For convenience, only first embodiment oral cannula 10 is employed for the description of the overall system. The description of the system applies equally to other embodiments of the oral cannula. Also, while not shown in the figures, an oxygen delivery line 920 from an oxygen source 925 can be split, such as by a Y-splitter or other type of valve, into both an oral cannula line and a nasal cannula line. The nasal cannula line can run to a conventional nasal cannula (not shown), and the oral cannula can simultaneously be used as described above. Such a configuration may be advantageous for situations in which a patient stops breathing through his nose but is still breathing through his mouth. An $ETCO_2$ sampling line 950 can be connected to a patient monitoring system 960. The $ETCO_2$ sampling line 950 can also be split.

As best shown in FIGS. 2A, 2B, and 3A through 3E, oxygen supply lumen 70 and $ETCO_2$ sampling lumen 80 in the first embodiment are in a co-sheath configuration in which $ETCO_2$ sampling lumen 80 is enclosed within oxygen supply lumen 70 to form a portion of oral cannula body 16. In this regard, the term "co-sheath" as used in this description refers to a structure in which one tube is contained within another, even if the axes of the tubes do not fall on the same line, including when inner tube is attached to an inner wall of the outer tube. The term "coaxial" as used in this description refers a structure in which tubes are oriented such that the longitudinal axes generally align, including when an inner tube is loose within the outer tube. A coaxial configuration is a subset of a co-sheath configuration.

Body 16 may be integrally formed with the tubing, or body 16 may be a unitary (that is, stand-alone) piece that has openings into which oxygen supply tubing 76 and $ETCO_2$ sampling tubing 86 fit and are attached (including by a separate connector 91 to mate the parts). The sidewall of body 16 includes plural apertures 36 that are in communication with the interior of lumen 70 and tubing 76 such that oxygen supplied by the oxygen source (illustrated in FIG. 10A) and controlled by the anesthetist or control system flows out of oral cannula 10 through apertures 36. Body 16 also includes apertures 37, 38 that are in fluid communication with plenum 74, sampling lumen 80, and tubing 86, such that sampling can be controlled by the $ETCO_2$ monitoring system In this regard, a distal end of oxygen supply lumen 70 is sealed by a bulkhead 72 such that a distal end of the oral cannula distal to the bulkhead forms a plenum 74, as best shown in FIG. 3A. The portion of the oral cannula including the bulkhead and plenum can be referred to as a tip, such as a cap, for example, a bulb. In this regard, the term "tip" in this disclosure is used broadly to refer to any end structure. The tips may be formed of rigid plastic sleeve. Alternatively, the tips may be formed of a soft plastic.

FIG. 3D is an enlarged view of a portion of the sidewall of the oxygen supply lumen 70 illustrating a configuration of apertures 36. In this regard, apertures 36 define a centerline that forms an angle A from a longitudinal centerline, which is horizontal as oriented in FIGS. 3D and 3E. Preferably, angle A is between 25 and 75 degrees, more preferably between 40 and 60 degrees, and most preferably between 45 and 50 degrees. Further, a distal or upper portion of apertures 36 include a scoop 92 intended to inhibit unintentional blocking of the apertures by contact with a patient's tissues.

The structure and function of the oral cannula described in this specification are for illustration purposes and are not intended to be limiting. Rather, it is intended that the claims be limited only to the express structure and function expressly stated in the claims. Further, features of the embodiments described above are not limited to the particular embodiment. Rather, the present invention encompasses any of the features described above in any combination.

What is claimed:

1. An oral cannula for placement within the oral cavity of a patient for delivery of a treatment gas and for collecting end-tidal carbon dioxide ($ETCO_2$), the oral cannula comprising:
   a treatment gas delivery lumen including at least one oropharyngeal aperture near a distal end of the treatment gas delivery lumen;
   an end-tidal $CO_2$ sampling lumen having an oropharyngeal end-tidal $CO_2$ inlet; and
   a cap including (i) a gas diverter adapted for diverting at least a portion of the treatment gas and (ii) an oropharyngeal end-tidal $CO_2$ inlet including flutes and apertures there between that are in communication with the end-tidal $CO_2$ sampling lumen, wherein the cap has a filter housing containing a hydrophobic filter element in the end-tidal $CO_2$ sampling lumen, the filter housing being rigid and thereby providing radial rigidity to the cap;
   wherein the oral cannula is adapted for custom bending or has a bend such that the oral cannula is insertable and retainable in a patient's mouth and functional for supplying a treatment gas directly into the oropharynx and sampling gas exhaled directly from the oropharynx of the patient.

2. The oral cannula of claim 1 wherein the gas diverter is a skirt at a periphery of the proximal end of the cap, the skirt forms a plenum into which the at least one aperture in the treatment gas delivery lumen opens, and the filter housing provides rigidity to the skirt to inhibit occlusion of the at least one aperture in the gas delivery lumen.

3. The oral cannula of claim 2 wherein the skirt is continuous about the cap.

4. The oral cannula of claim 1 wherein the cap includes a body and a funnel that is housed within the body, and the filter housing is mounted to the funnel.

5. The oral cannula of claim 1 wherein the cap includes an end-tidal $CO_2$ sampling channel between the end-tidal $CO_2$ inlets and the end-tidal $CO_2$ sampling lumen, the filter element being disposed in the end-tidal $CO_2$ sampling channel.

6. The oral cannula of claim 5 wherein the rigid filter housing is adapted for resisting occlusion of the end-tidal $CO_2$ sampling lumen channel.

7. The oral cannula of claim 5 wherein the cap includes a sampling recess and a delivery recess on a proximal end thereof, the end-tidal $CO_2$ sampling lumen being located in the sampling recess, the treatment gas delivery lumen being located in the delivery recess.

8. The oral cannula of claim 5 wherein the cap is cylindrical, the flutes form the distal-most portion of the cap, and the filter element is at a base of the flutes.

9. The oral cannula of claim 1 further comprising a shaping wire that is adapted for repeated plastic bending by a user's hands to conform to a desired shape or contour of a patient's facial, oral cavity, or airway anatomy.

10. The oral cannula of claim 9 wherein the wire is encased and is formed of a non-magnetic material.

11. The oral cannula of claim 9 wherein the wire has sufficient strength to enable a user to insert the oral cannula through and past the oral cavity.

12. The oral cannula of claim 1 wherein the at least one aperture of the gas delivery lumen is located in a sidewall of the gas delivery lumen, and the gas delivery lumen has a sealed tip.

13. The oral cannula of claim 1 wherein the end-tidal $CO_2$ inlet is distal relative to the gas diverter.

14. The method of claim 1 wherein the gas diverter is a skirt at a periphery of the proximal end of the cap, the skirt forms a plenum into which the at least one aperture in the treatment gas delivery lumen opens, and the filter housing provides rigidity to the skirt to inhibit occlusion of the at least one aperture in the gas delivery lumen.

15. The method of claim 14 wherein the skirt is continuous about the cap.

16. A method of administering a treatment gas and sampling end-tidal $CO_2$ for a patient, comprising the steps of:
inserting the oral cannula of claim 1 into a patient's mouth,
providing treatment gas through the treatment gas delivery lumen, through an at least one oropharyngeal aperture in the treatment gas delivery lumen, and via the gas diverter; and
drawing an exhaled gas through an oropharyngeal end-tidal $CO_2$ inlet and through an end-tidal $CO_2$ sampling lumen, wherein the oral cannula has a cap having a filter housing containing a hydrophobic filter element in the end-tidal $CO_2$ sampling lumen, the filter housing being rigid and thereby providing radial rigidity to the cap.

17. The method of claim 16 wherein the cap includes a body and a funnel that is housed within the body, and the filter housing is mounted to the funnel.

18. The method of claim 16 wherein the cap includes an end-tidal $CO_2$ sampling channel between the end-tidal $CO_2$ inlets and the end-tidal $CO_2$ sampling lumen, the filter element being disposed in the end-tidal $CO_2$ sampling channel.

19. The method of claim 18 wherein the rigid filter housing is adapted for resisting occlusion of the end-tidal $CO_2$ sampling lumen channel.

20. The method of claim 18 wherein the cap includes a sampling recess and a delivery recess on a proximal end thereof, the end-tidal $CO_2$ sampling lumen being located in the sampling recess, the treatment gas delivery lumen being located in the delivery recess.

21. The method of claim 18 wherein the cap is cylindrical, the flutes form the distal-most portion of the cap, and the filter element is at a base of the flutes.

22. The method of claim 16 wherein the oral cannula further comprises a shaping wire that is adapted for repeated plastic bending by a user's hands to conform to a desired shape or contour of a patient's facial, oral cavity, or airway anatomy.

23. The method of claim 22 wherein the wire is encased and is formed of a non-magnetic material.

24. The method of claim 22 wherein the wire has sufficient strength to enable a user to insert the oral cannula through and past the oral cavity.

25. The method of claim 16 wherein the at least one aperture of the gas delivery lumen is located in a sidewall of the gas delivery lumen, and the gas delivery lumen has a sealed tip.

26. The method of claim 16 wherein the end-tidal $CO_2$ inlet is distal relative to the gas diverter.

* * * * *